(12) United States Patent
Bronich et al.

(10) Patent No.: US 9,498,533 B2
(45) Date of Patent: Nov. 22, 2016

(54) DRUG DELIVERY COMPOSITIONS AND METHODS

(75) Inventors: Tatiana K. Bronich, Omaha, NE (US); Alexander V. Kabanov, Chapel Hill, NC (US); Jong Oh Kim, Syeongsan-buk-do (KR)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 14/001,084

(22) PCT Filed: Apr. 4, 2012

(86) PCT No.: PCT/US2012/032128
§ 371 (c)(1),
(2), (4) Date: Oct. 17, 2013

(87) PCT Pub. No.: WO2012/138730
PCT Pub. Date: Oct. 11, 2012

(65) Prior Publication Data
US 2014/0039068 A1 Feb. 6, 2014

Related U.S. Application Data

(60) Provisional application No. 61/471,492, filed on Apr. 4, 2011.

(51) Int. Cl.
*A61K 47/34* (2006.01)
*A61K 31/704* (2006.01)
*A61K 9/107* (2006.01)

(52) U.S. Cl.
CPC ............ *A61K 47/34* (2013.01); *A61K 9/1075* (2013.01); *A61K 31/704* (2013.01)

(58) Field of Classification Search
USPC ....................................... 514/772.1
See application file for complete search history.

(56) References Cited

U.S. PATENT DOCUMENTS

| | | | |
|---|---|---|---|
| 4,808,314 A | 2/1989 | Karplus et al. | |
| 6,333,051 B1 | 12/2001 | Kabanov et al. | |
| 6,383,500 B1 | 5/2002 | Wooley et al. | |
| 7,056,532 B1 * | 6/2006 | Kabanov et al. | 424/486 |
| 7,169,411 B1 | 1/2007 | Kabanov et al. | |
| 7,217,770 B2 * | 5/2007 | Seo et al. | 525/419 |
| 7,332,527 B2 | 2/2008 | Bronich et al. | |
| 8,168,222 B2 | 5/2012 | Kabanov et al. | |
| 2002/0136769 A1 | 9/2002 | Kabanov et al. | |
| 2003/0009004 A1 | 1/2003 | Nam et al. | |
| 2003/0083299 A1 | 5/2003 | Ferguson et al. | |
| 2006/0240092 A1 | 10/2006 | Breitenkamp et al. | |
| 2007/0059271 A1 | 3/2007 | Kataoka et al. | |
| 2008/0145416 A1 | 6/2008 | Bronich et al. | |
| 2008/0319375 A1 | 12/2008 | Hardy | |
| 2010/0291065 A1 | 11/2010 | Kabanov et al. | |

FOREIGN PATENT DOCUMENTS

| | | |
|---|---|---|
| WO | 9856334 | 12/1998 |
| WO | 9856348 | 12/1998 |
| WO | 03030941 | 4/2003 |
| WO | 03063827 | 8/2003 |
| WO | 2005084410 | 9/2005 |
| WO | 2006097793 | 9/2006 |
| WO | 2009/021728 | 2/2009 |

OTHER PUBLICATIONS

Lavasanifar et al. Advance Drug Delivery Reviews 54 (2002) 169-190.*
Lee et al. (Biomolecules 12, 1224-1233 (2011).*
Rosler, A., et al. "Advanced drug delivery devices via self-assembly of amphiphilic block copolymers." Adv Drug Deliv Rev. Dec. 3, 2001;53(1):95-108.
Bronich, T.K., et al., "Polymer Micelle with Cross-Linked Ionic Core," J. Am. Chem. Soc., 2005, 8236-8237, 127.
Vinogradov, S.V., et al."Polyion Complex Micelles with Protein-Modified Corona for Receptor-Mediated Delivery of Oligonucleotides into Cells." Bioconjugate Journal, 1999, 851-860, 10(5).
Klyachko, N.L., et al., "Cross-linked antioxidant nanozymes for improved delivery to CNS," 2012, 119-129, 8(1).
Wu, J., et al."Quantitative Evaluation of Monocyte Transmigration into the Brain Following Chemical Opening of the Blood-Brain Barrier in Mice." Brain Research, 2006, 79-85, 1098(1).
Ballabh, P., et al. "The Blood-Brain Barrier: An Overview Structure, Regulation, and Clinical Implications." Neurobiology of Disease, 2004, 1-13, 16(1).
Kakizawa, Y., et al. Block copolymer micelles for delivery of gene and related compounds. • Advanced Drug Delivery Reviews, 2002, 203-222, 54(2).
Aktas, Y., et al. "Development and Brain Delivery of Chitosan-PEG Nanoparticles Functionalized with the Monoclonal Antibody OX26." Bioconjugate Journal, 2005, 1503-1511, 16(6).
Vinogradov, S.V., et al."Nanogels for oligonucleotide delivery to the brain," Bioconjug Chem., 2004, 50-60, 15 (1).
Jaturanpinyo, M.,et al. "Preparation of bionanoreactor based on core-shell structured polyion complex micelles entrapping trypsin in the core cross-linked with glutaraldehyde," Bioconjug Chem., 2004, 344-348, 15(2).
Harada, A., et al. "Novel Plyion Complex Micelles Entrapping Enzyme Molecules in the Core: Preparation of Narrowly-Distributed Micelles from Lysozyme and Poly(ethylene glycol)-Poly(aspartic acid) Block Copolymer in Aqueous Medium," Macromolecules, 1998, 288-294, 31.
Harada, A., et al."Formation of Polyion Complex Micelles in an Aqeous Milieu from a Pair of Oppositely-Charged Block Copolymers with Poly(ethylene glycol) Segments," Macromolecules, 1995, 5294-5299, 25.
Pardridge, W.M. "The blood-brain barrier and neurotherapeutics," NeuroRx, 2005, 1-2, 2(1).

(Continued)

Primary Examiner — Shirley V Gembeh
(74) Attorney, Agent, or Firm — Robert C. Netter, Jr.; Dann, Dorfman, Herrell & Skillman

(57) ABSTRACT

The present invention provides compositions and methods for the delivery of therapeutics to a cell or subject.

17 Claims, 19 Drawing Sheets

(56) References Cited

OTHER PUBLICATIONS

Figure 1:
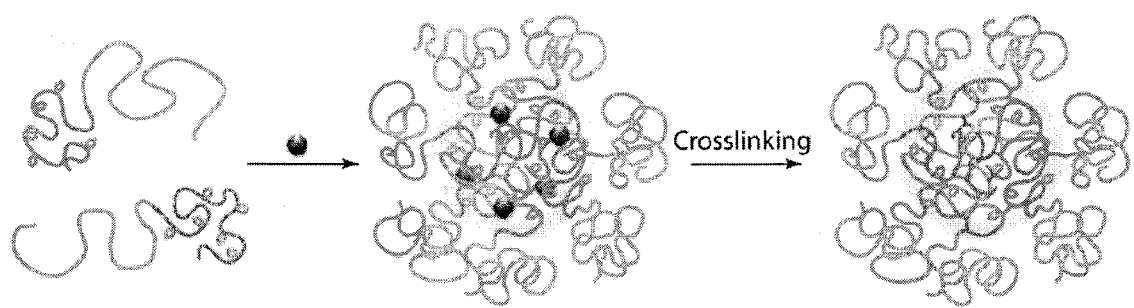
Figure 1:
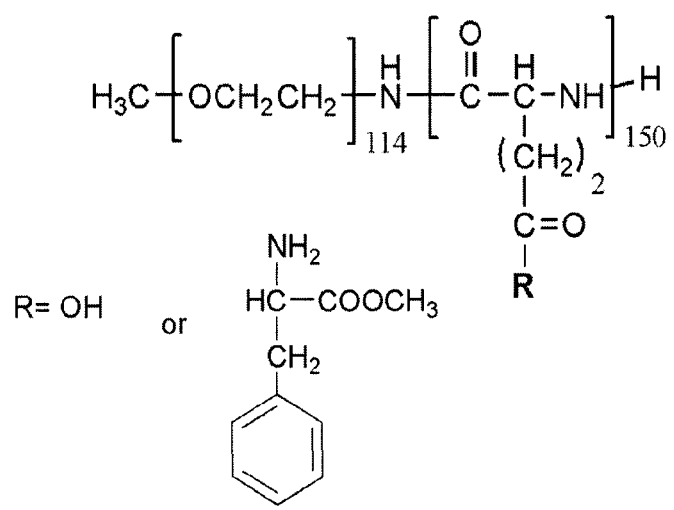

Kim, J.O., et al., "Polymer Micelles with Cross-Linked Polyanion Core for Delivery of a Cationic Drug Doxorubicin," J. Control Release, 2009, 197-204, 138(3).
Doctor, B.P., et al."Bioscavengers for the protection of humans against organophosphate toxicity," Chem Biol Interact., Epub Nov. 15, 2005, 167-171, 157-158.
Harada, A., et al. "Pronounced activity of enzymes through the incorporation into the core of polyion complex micelles made from charged block copolymers," J. Control Release, 2001, 85-91, 72(1-3).
Dou, H., et al. "Development of a macrophage-based nanoparticle platform for antiretroviral drug delivery." Blood, 2006, 2827-2835, 108(8).
Dou, H., et al. "Laboratory investigations for the morphologic, pharmacokinetic, and anti-retroviral properties of indinavir nanoparticles in human monocyte-derived macrophages." Virology, 2007, 148-158, 358(1).
Vinogradov, S.V., et al. "Nanosized cationic hydrogels for drug delivery: preparation, properties and interactions with cells." Adv Drug Deliv Rev. 2002, 135-147, 54(1).
Kim, J.O., et al., "Block Ionomer Complex Micelles with Cross-Linked Cores for Drug Delivery," Polm. Sci. Ser. A. Chem. Phys., 2009, 708-718, 51(6).
Harada, A., et al. "Switching by pulse electric field of the elevated enzymatic reaction in the core of polyion complex micelles." J Am Chem Soc., 2003, 15306-15307, 125(50).
Batrakova, E.V., et al. "A macrophage-nanozyme delivery system for Parkinson's disease," Bioconjug Chem. 2007, 1498-1506, 18(5).
Oberoi H.S., et al., "Core Cross-Linked Block Ionomer Micelles as pH-Responsive Carriers for cis-Diamminedichloroplatinum(II)," J. Control Release, 2011, 64-72, 153(1).
Kabanov A.V., et al., "Soluble Stoichiometric Complexes from Poly(N-ethyl-4-vinylpyridinium) Cations and Poly (ethylene oxide)-block-polymethacrylate Anions," Macromolecules, 1996, 6797-6802, 29.
Bronich, T.K., et al., "Soluble Complexes from Poly(ethylene oxide)-block-polymethacrylate Anions and N-Alkylpyridinium Cat•ions," Macromolecules, 1997, 3519-3525, 30.
Kabanov, A.V., et al., Kabanov, Alexander V. et al. "Spontaneous Formation of Vesicles from Complexes of Block Ionomers and Surfactants," J Am. Chem. Soc. 1998, 9941-9942, 120.
Bronich, T.K., et al., "Self-Assembly in Mixtures of Poly(ethylene oxide)-graft-Poly(ethylene imine) and Alkyl Sulfates," Langmuir, 1998, 6101-6106, 14.
Bronich, T.K., et al., "Novel drug delivery systems based on the complexes of block ionomers and surfactants of opposite charge," Colloids and Surfaces B: Biointerfaces, 1999, 243-251, 16.
Bronich, T.K., et al., "Effects of Block Length and Structure of Surfactant on Self-Assembly and Solution Behavior of Block Ionomer Complexes," Langmuir, 2000, 481-489, 16.
Bronich, T.K., et al., "Interaction of Nanosized Copolymer Networks with Oppositely Charged Amphiphilic Molecules," Nano Letters, 2001, 535-540, 1.
Kim, J.O., et al., "Polymeric Micelles with Ionic Cores Containing Biodegradable Crosslinks for Delivery of Chemotherapeutic Agents," Biomacromolecules, 2010, 919-926, 11(4).
Bronich, T.K., et al.,"Synthesis of Vesicles on Polymer Template," J Am. Chem. Soc., 2002, 11872-11873.
Lysenko, E.A., et al., "Block Ionomer Complexes with Poly•styrene Core-Forming Block in Selective Solvents of Various Polarities. 2. Solution Behavior and Self-Assembly in Nonpolar Solvents," Macromolecules, 2002, 6344-6350, 35.
Han, M.J., et al., "Synthesis, Characterization, and Biological Activity of Polyanion-cis-diannnineplatinum(II) Complexes as Antitumor Agents," Journal of Bioactive and Compatible Polymers, 1992, 358-369, 7.
Bogdanov, A., et al., "An Adduct of cis-Diam•minedichlorophatinum(II) and Poly(ethylene glycol)poly(L-lysine)• Succinate: Synthesis and Cytotoxic Properties," Bioconjugate Chem., 1996, 144-149, 7.
Bogdanov, A., et al., "A Long-Circulating Co-Polymer in "Passive Targeting" to Solid Tumors," Journal of Drug Targeting, 1997, 321-330, 4.
Yokoyama, M., et al., "Introduction of cisplatin into polymeric micelle," Journal of Controlled Release,1996, 351-356, 39.
Nishiyama, N., et al. "Preparation and Characterization of Self-Assembled Polymer-Metal Complex Micelle from cis•Dichlorodiannnineplatinum(II) and Poly(ethylene-glycol)-Poly(af:I•aspartic acid) Block Copolymer in an Aqueous Medium," Langmuir, 1999, 377-383, 15.
Mizumura, Y., et al. "Cisplatin-incorporated Polymeric Micelles Eliminate Nephrotoxicity, While Maintaining Antitumor Activity," Jpn. J Cancer Res., 2001, 328-336, 92.
Nishiyama, N., et al. "Preparation and characterization of size-controlled polymeric micelle containing cis-dichlorodiam•mineplatinum(II) in the core," Journal of Controlled Release, 2001, 83-94, 74.
Nukolova N.V., et al., "Polyelectrolyte Nanogels Decorated with Monoclonal Antibody for Targeted Drug Delivery," React. Funct. Polym., 2011, 315-323, 71(3).

* cited by examiner

(C) *cl*-PEO-*b*-PPGA50

DRUG DELIVERY COMPOSITIONS AND METHODS

This application is a §371 application of PCT/US2012/032128, filed Apr. 4, 2012, which claims priority under 35 U.S.C. §119(e) to U.S. Provisional Patent Application No. 61/471,492, filed Apr. 4, 2011. The foregoing applications are incorporated by reference herein.

This invention was made with government support under Grant No. 1RO1 CA116591-01A1 awarded by the National Institutes of Health. The government has certain rights in the invention.

FIELD OF THE INVENTION

The present invention relates generally to the delivery of compounds. More specifically, the present invention relates to compositions and methods for the delivery of bioactive agents such as therapeutic agents to a patient, particularly for the treatment of a disease or disorder.

BACKGROUND OF THE INVENTION

A variety of self-assembled polymer micelles using block copolymers has been extensively explored as effective drug delivery carriers for anti-cancer drugs (Alakhov et al. (1999) Coll. Surfaces B: Biointerfaces, 16:113-134; Bronich et al. (1999) Coll. Surfaces B: Biointerfaces, 16:243-251; Allen et al. (1999) Coll. Surfaces B: Biointerfaces, 16:3-27; Nakanishi et al. (2001) J. Control Release, 74:295-302; Lavasanifar et al. (2002) Adv. Drug Deliv. Rev., 54:169-190; Carlsen et al. (2009) Curr. Opin. Coll. Interface Sci., 14:329-339; Kabanov et al. (2009) Angew Chem. Int. Ed. Engl., 48:5418-5429). Nanoscale polymer micelles have predominant features such as long blood circulation time, avoidance of renal excretion and passive targeting via enhanced permeability and retention effect (EPR effect) (Maeda, H. (2001) Adv. Enzyme Regul., 41:189-207). However, many nanoscale polymer micelles lack stability and can leak the bioactive agent quickly when administered to a subject. To avoid the negative side effects associated with the premature release of the bioactive agent, micelles of greater stability are desired. Additionally, micelles capable of delivering more than one compound (e.g., a hydrophobic and a charged compound) at the same time are also desired to deliver synergistic effects.

SUMMARY OF THE INVENTION

In accordance with the instant invention, polymer micelles are provided. In a particular embodiment, the micelle comprises at least one block copolymer comprising an ionically charged polymeric segment and a non-ionically charged polymeric segment, wherein the ionically charged polymeric segment is grafted with hydrophobic moieties. The hydrophobized ionically charged polymeric segment forms the core of the micelle and the non-ionically charged polymeric segment is hydrophilic and forms the shell of the micelle. For stability, the core of the micelle is cross-linked. In a particular embodiment, the micelle further comprises at least one bioactive agent such as a therapeutic agent or a chemotherapeutic agent. Compositions comprising the micelles of the instant invention are also provided.

In accordance with another aspect of the instant invention, methods for treating, inhibiting, and/or preventing a disease or disorder in a subject are provided. In a particular embodiment, the method comprises administering to the subject at least one micelle of the instant invention. The methods may further comprise the administration of other therapeutic methods or compositions to the subject. In a particular embodiment, the disease or disorder is cancer and the micelles encapsulate at least one chemotherapeutic agent, particularly at least two wherein the two chemotherapeutic agents act synergistically.

In accordance with another aspect of the instant invention, methods of synthesizing micelles of the instant invention are provided. In a particular embodiment, the method comprises hydrophobizing the ionically charged polymeric segment of a block copolymer comprising an ionically charged polymeric segment and a non-ionically charged polymeric segment; neutralizing the ionically charged polymeric segment with moieties of opposite charge, thereby allowing for self-assembly of polymer micelles; cross-linking the neutralized ionically charged polymeric segment; and removing the moieties of opposite charge and unreacted cross-linker. The method may further comprise incorporating at least one bioactive agent into the core of the micelle.

BRIEF DESCRIPTIONS OF THE DRAWING

FIG. 1 provides a scheme of the synthesis of cross-linked PEO-b-PPGA micelles.

Figure 2:
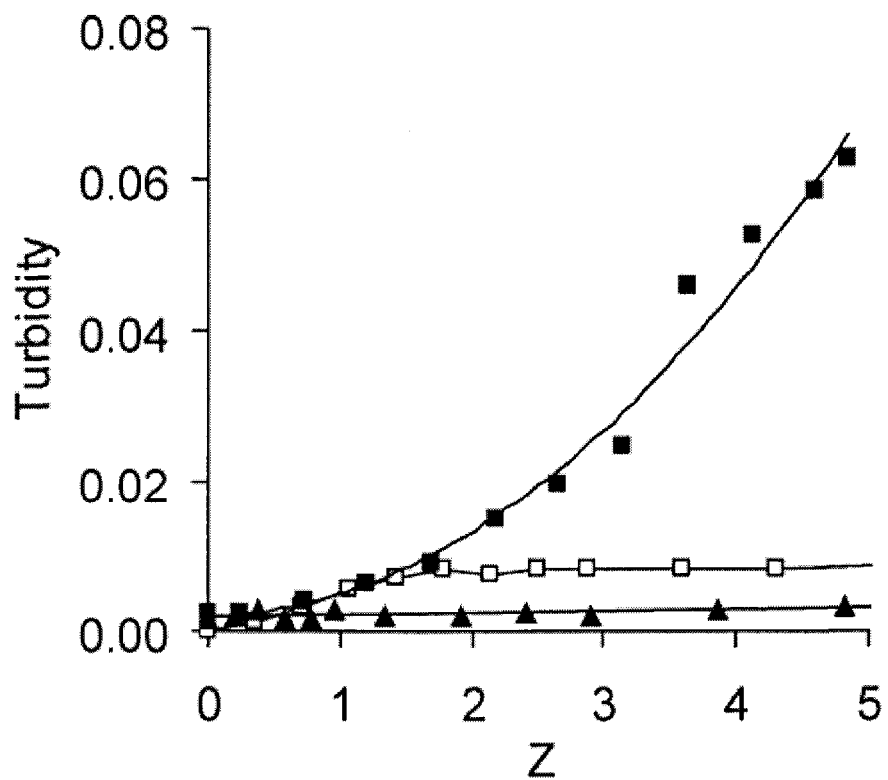

FIG. 2 provides a graph of turbidity in the PEO-b-PGA/$Ca^{2+}$ mixtures as a function of the charge ratio in the mixture, Z. (▲) PEO-b-PGA/$Ca^{2+}$, (□) PEO-b-PPGA25/$Ca^{2+}$ and (■) PEO-b-PPGA50/$Ca^{2+}$.

Figure 3:
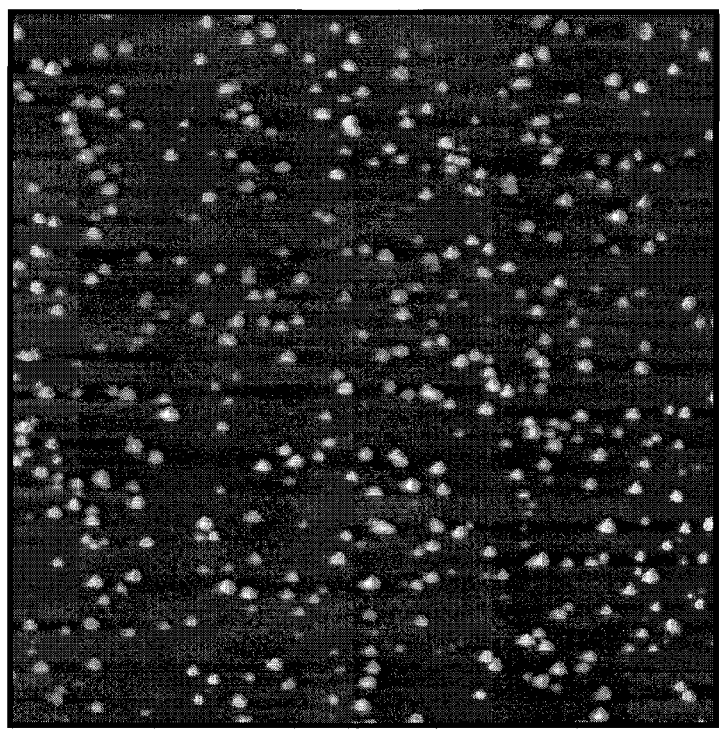
Figure 3:
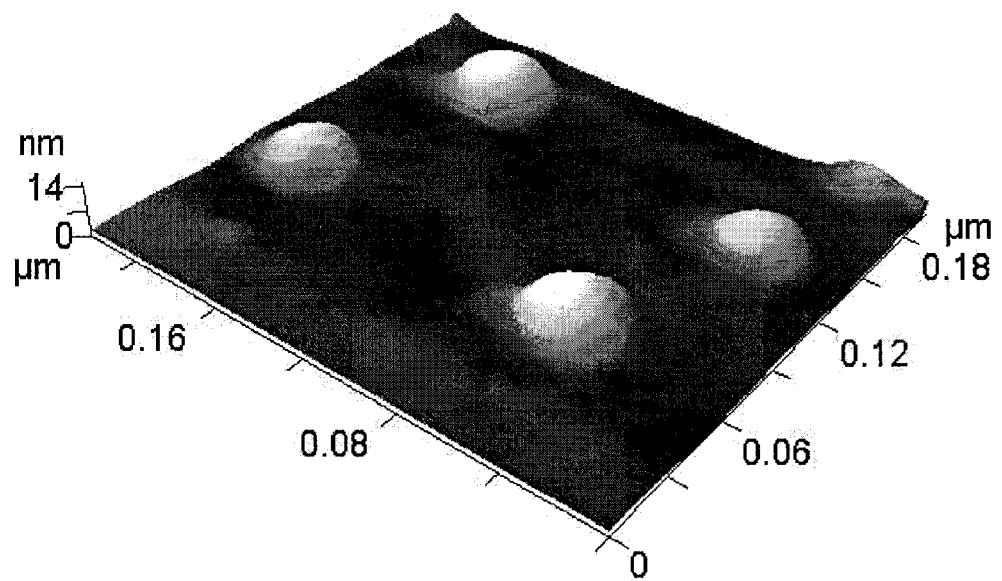

FIG. 3 provides tapping mode AFM images of cl-PEO-b-PPGA50 micelles in air. Targeted degree of cross-linking is 20%. Scan size in 2 μm.

Figure 4:
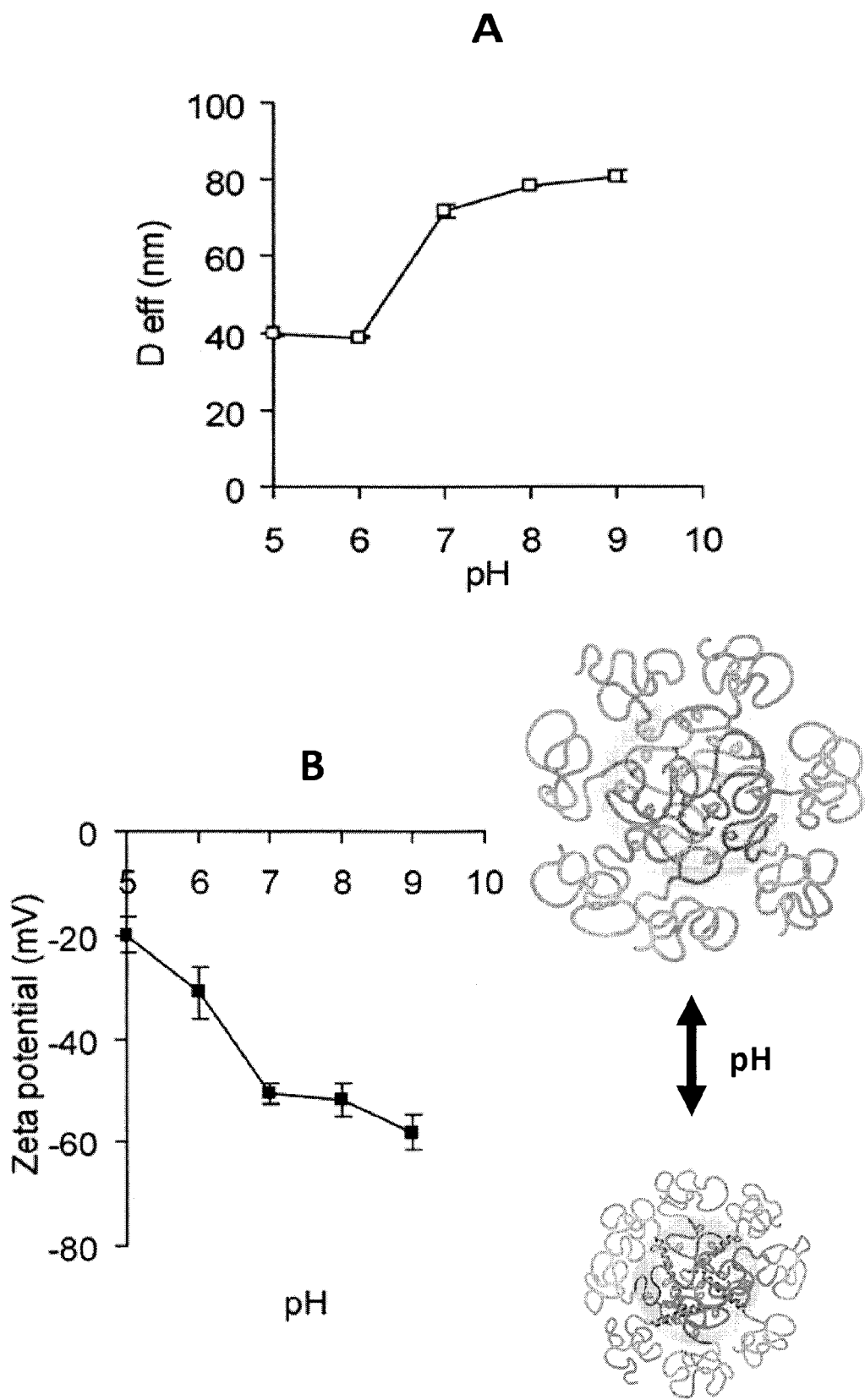

FIG. 4 shows the physicochemical characterization of cl/-PEO-b-PPGA50 micelles. FIG. 4 provides a graph of the effective diameter ($D_{eff}$) (FIG. 4A) and ζ-potential (FIG. 4B) with 20% targeted degree of cross-linking as a function of pH.

Figure 5:
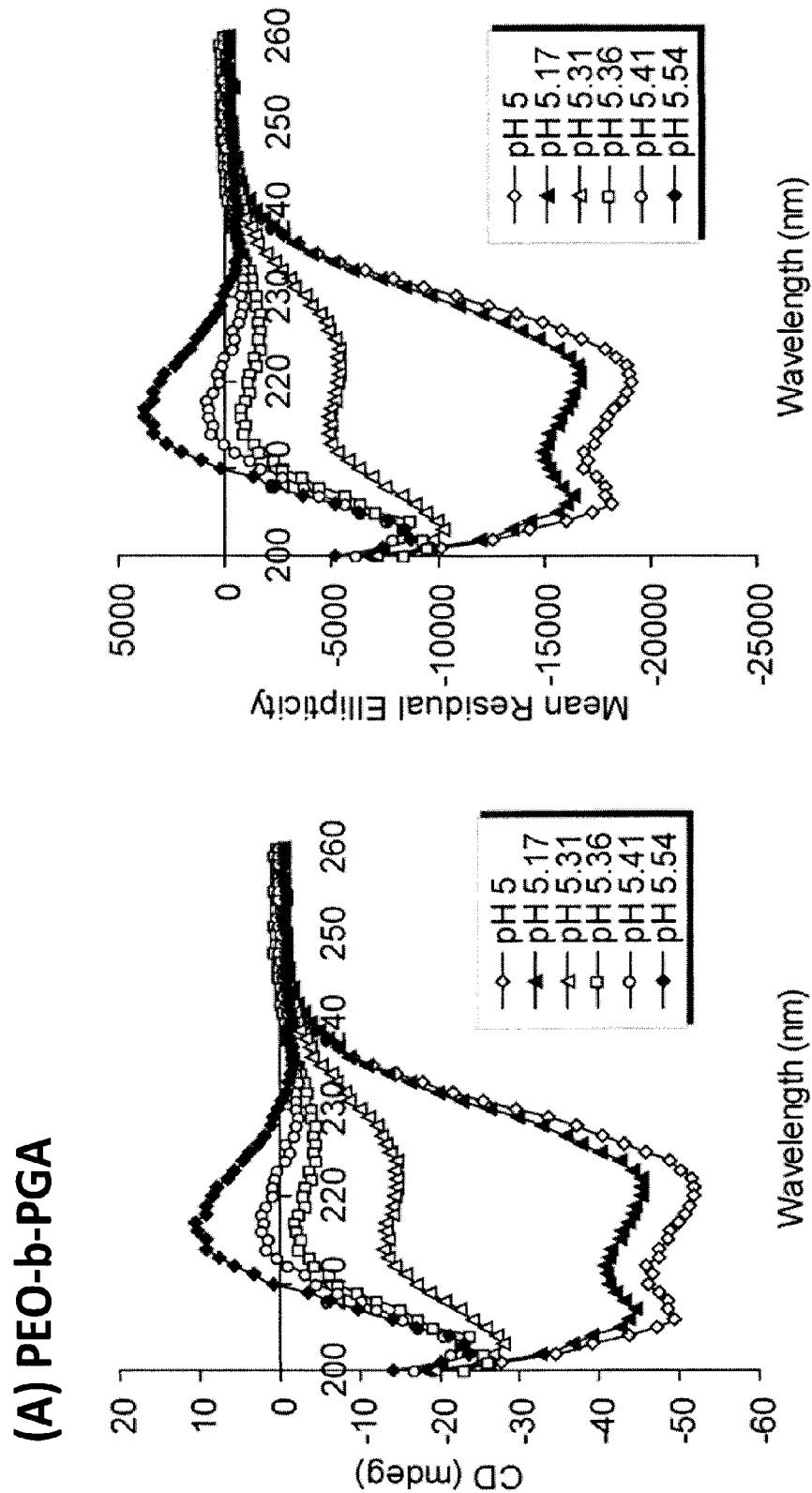
Figure 5:
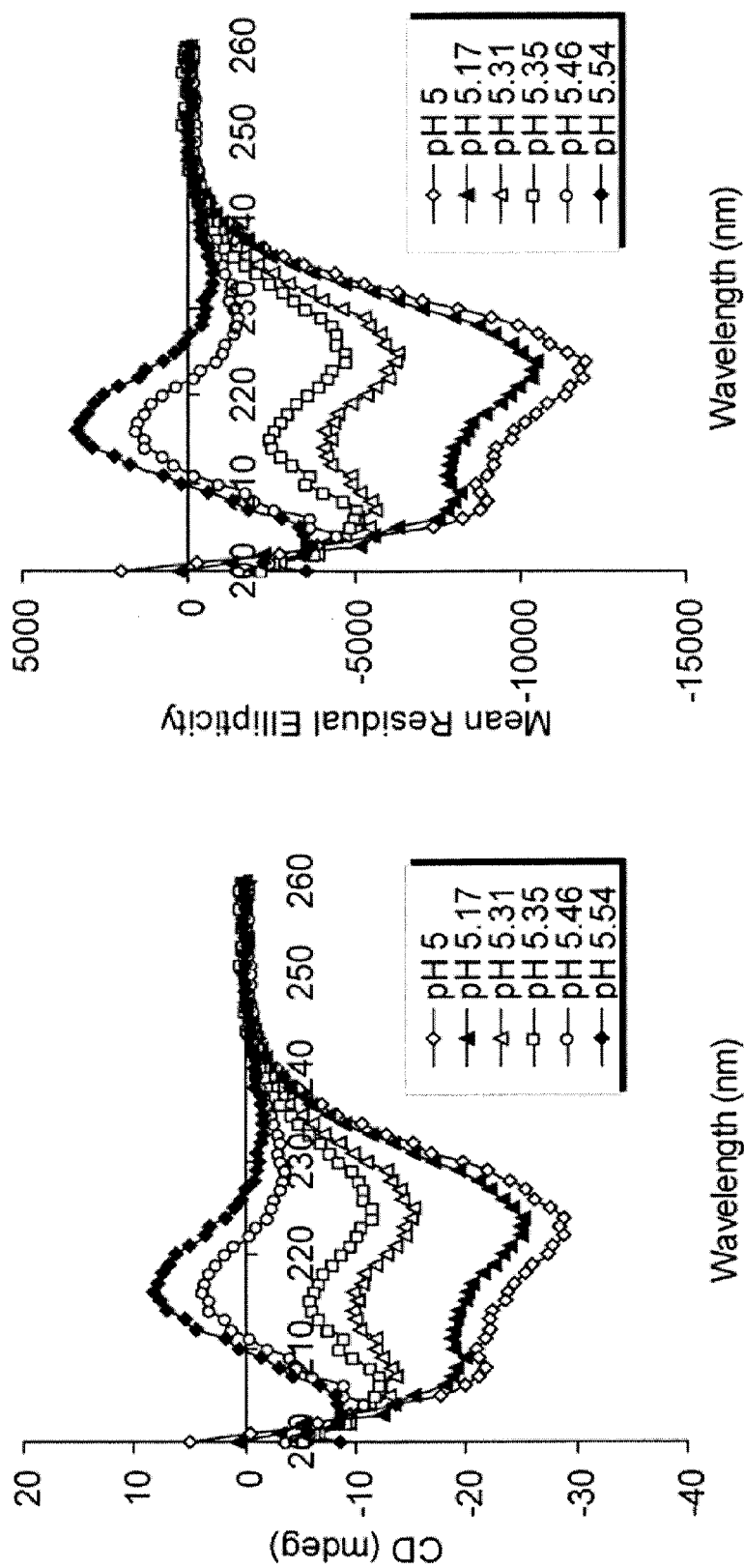
Figure 5:
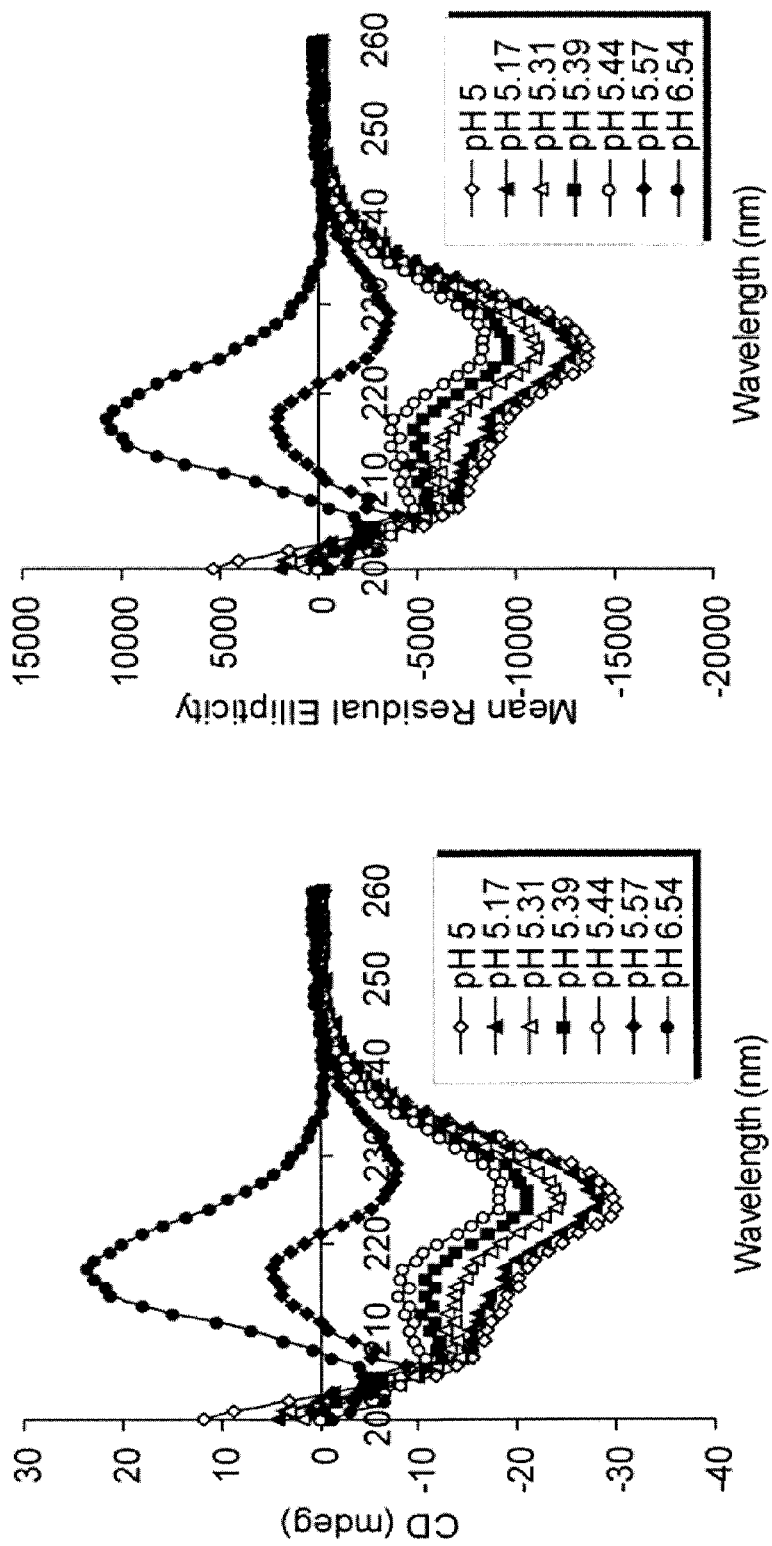

FIG. 5 provides CD spectra and mean residual ellipticity (MRE) of PEO-b-PGA (FIG. 5A), PEO-b-PPGA25 (FIG. 5B), and PEO-b-PPGA50 (FIG. 5C).

Figure 6:
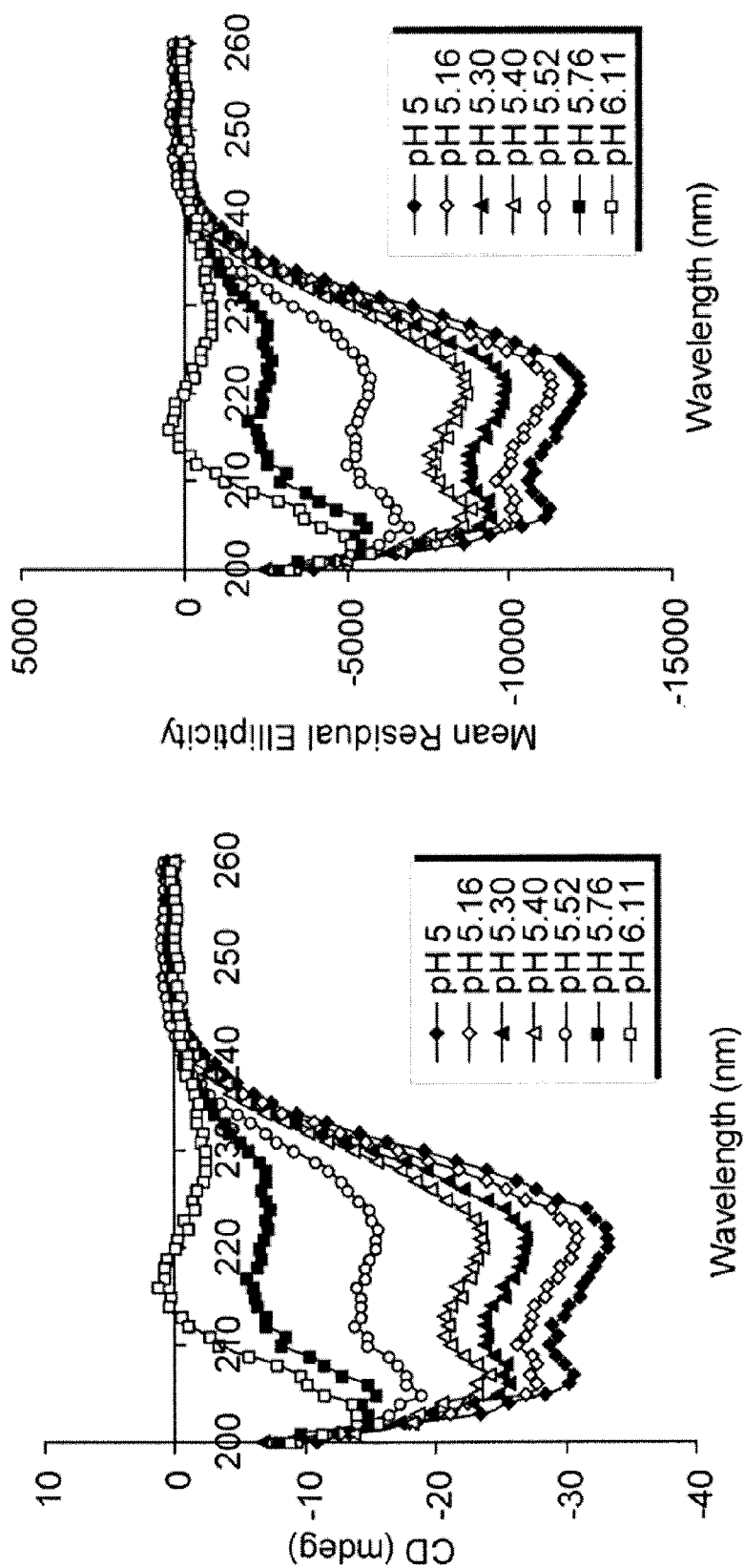
Figure 6:
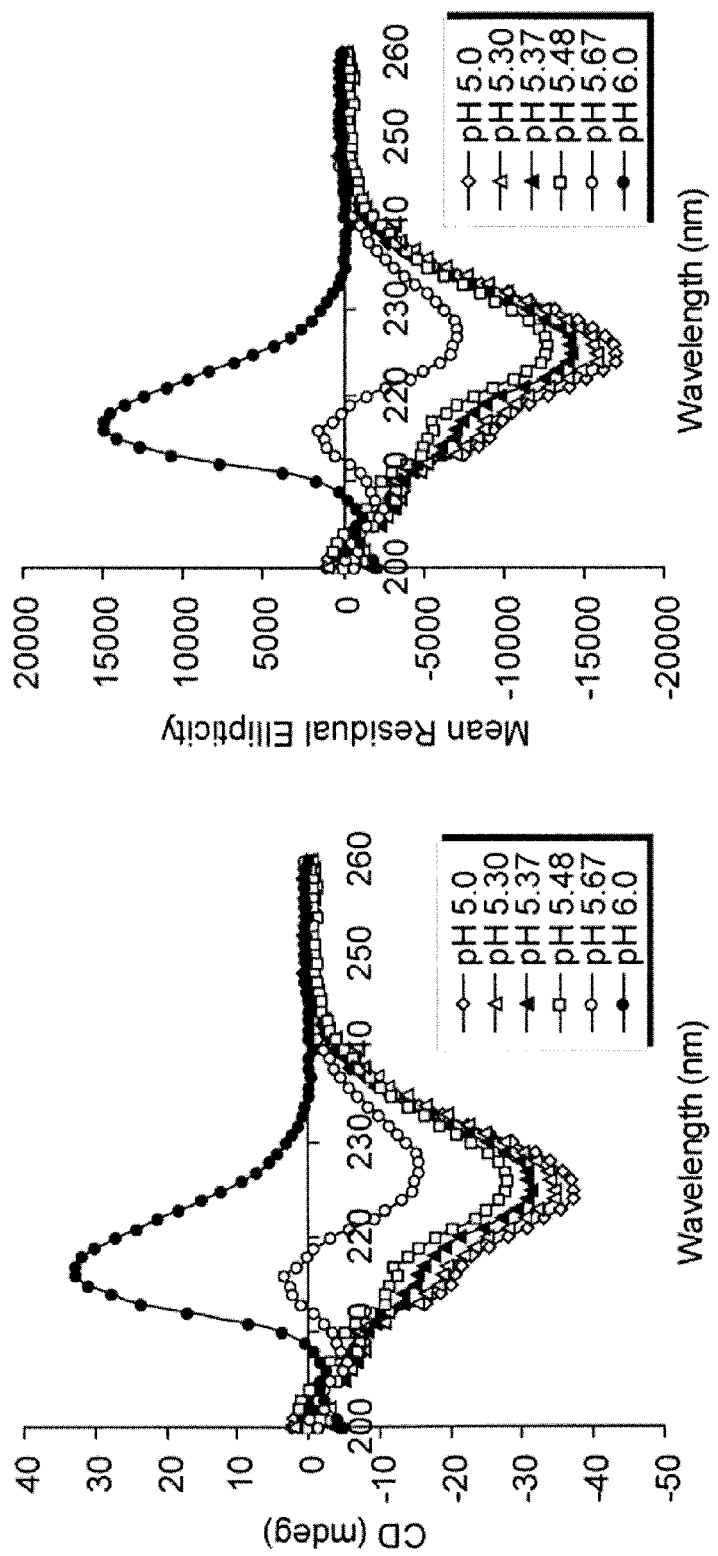

FIG. 6 CD spectra and MRE of PGA-based cl-micelles, namely cl-PEO-b-PGA (FIG. 6A) and cl-PEO-b-PPGA50 (FIG. 6B).

Figure 7:
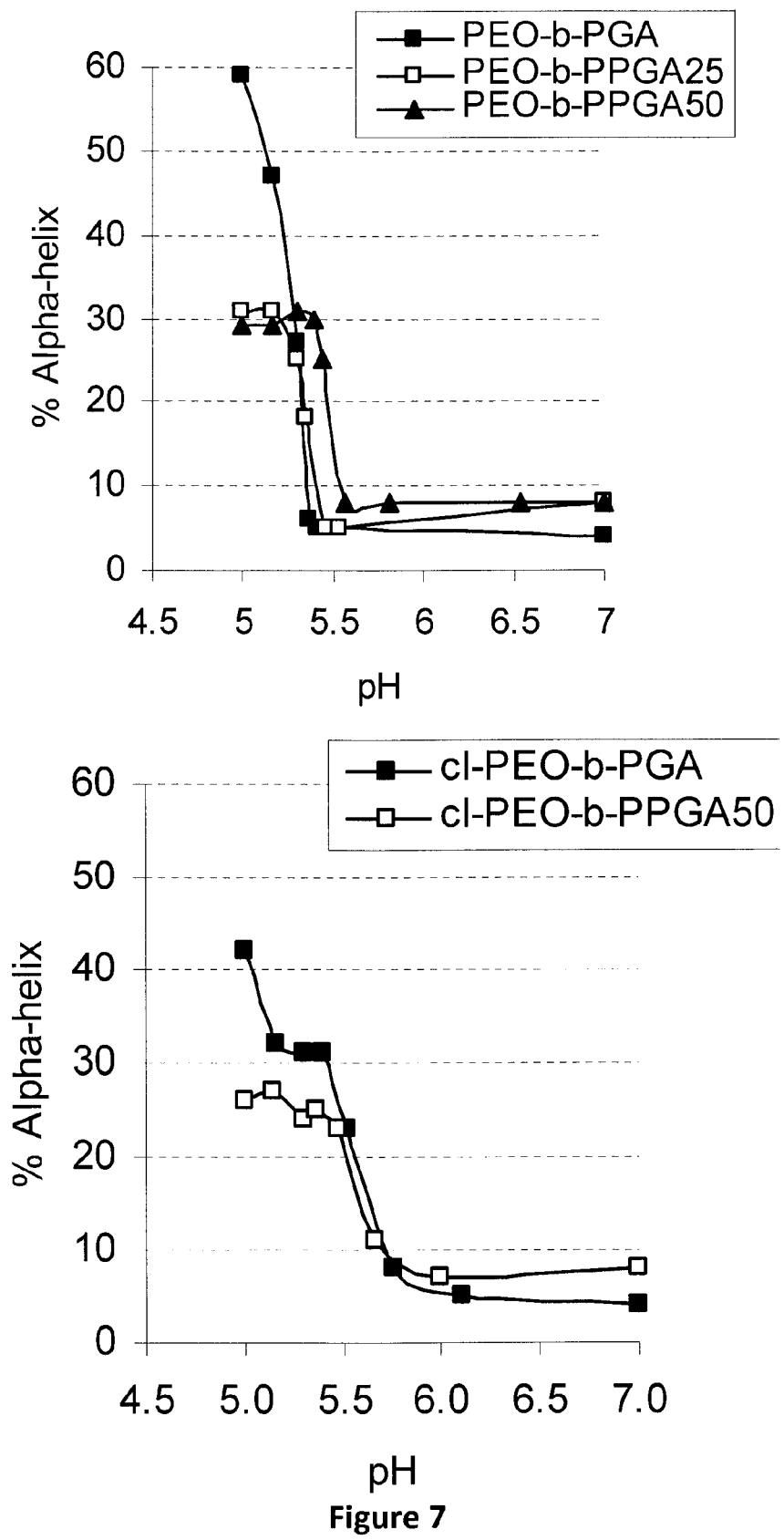

FIG. 7 provides graphs showing the effect of pH on alpha-helix (%) of PGA-based copolymers and cl-micelles.

Figure 8:
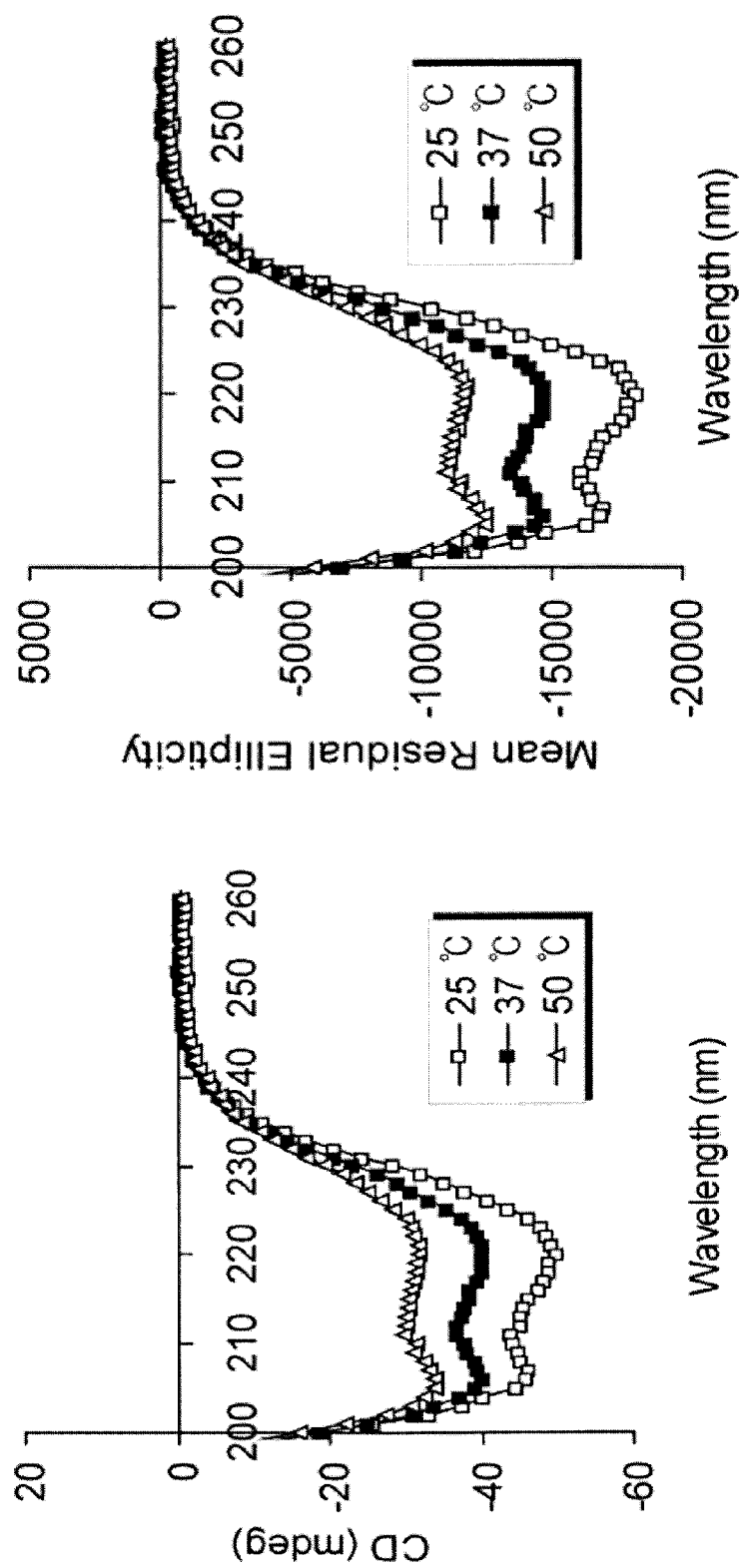
Figure 8:
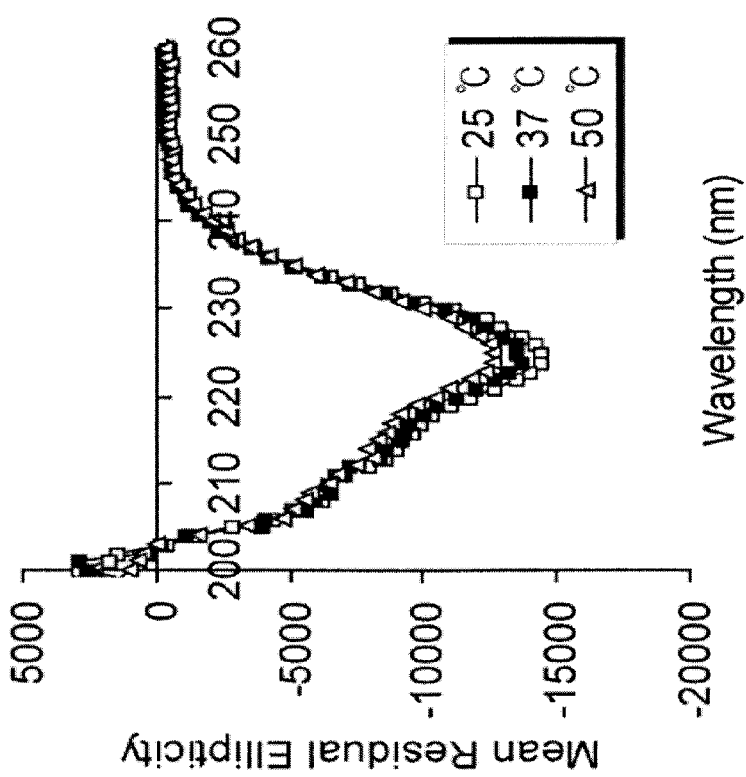
Figure 8:
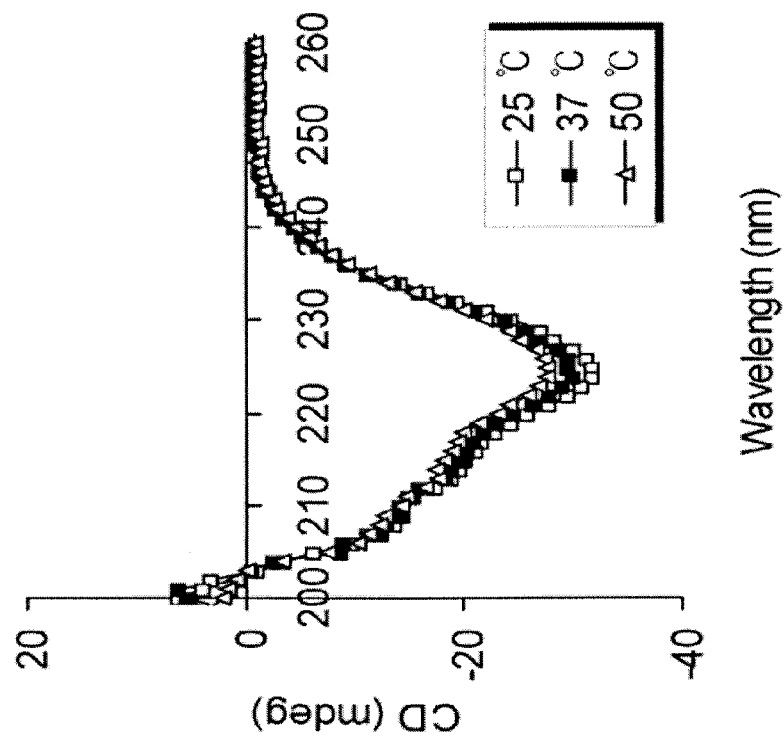
Figure 8:
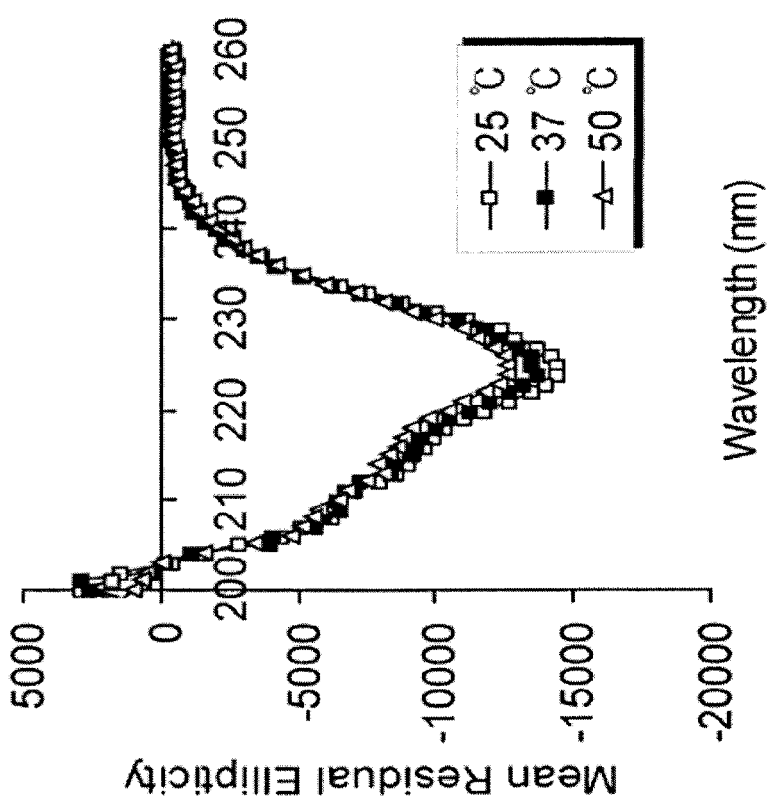
Figure 8:
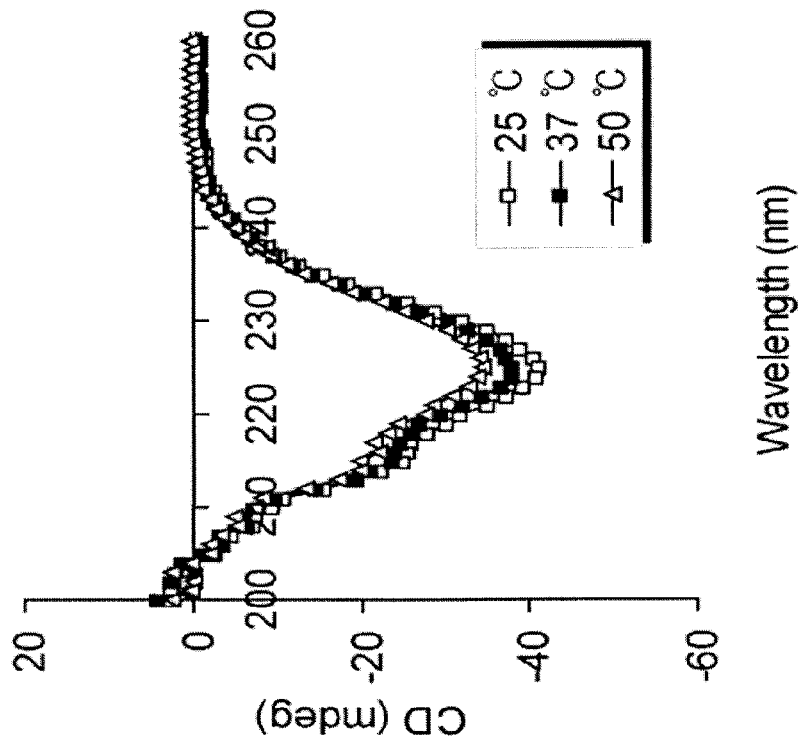

FIG. 8 provides graphs showing the effect of temperature on CD spectra of various PGA-based copolymers at pH 5.0, namely PEO-b-PGA (FIG. 8A), PEO-b-PPGA50 (FIG. 8B), and cl-PEO-b-PPGA50 (FIG. 8C).

Figure 9:
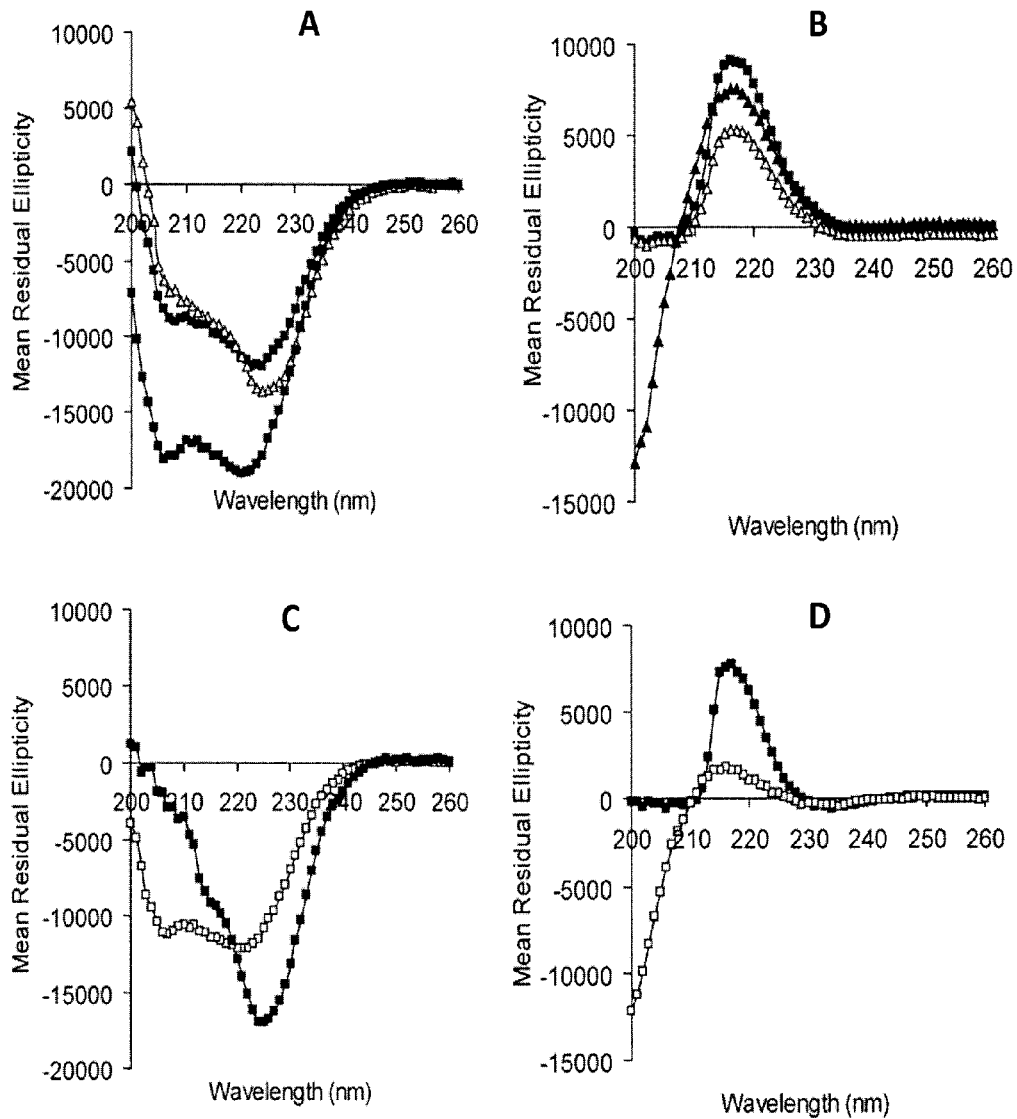

FIG. 9 provides graphs of the mean residual ellipticity of PGA-based polymers (FIGS. 9A, 9B) and cl-micelles (FIGS. 9C, 9D) at pH 5 (FIGS. 9A, 9C) and at pH 7.0 (FIGS. 9B, 9D) at 25° C. In FIGS. 9A and 9B, (■) PEO-b-PGA, (▲) PEO-b-PPGA25 and (Δ) PEO-b-PPGA50. In FIGS. 9C and 9D, (□) cl-PEO-b-PGA and (■) cl-PEO-b-PPGA50.

Figure 10:
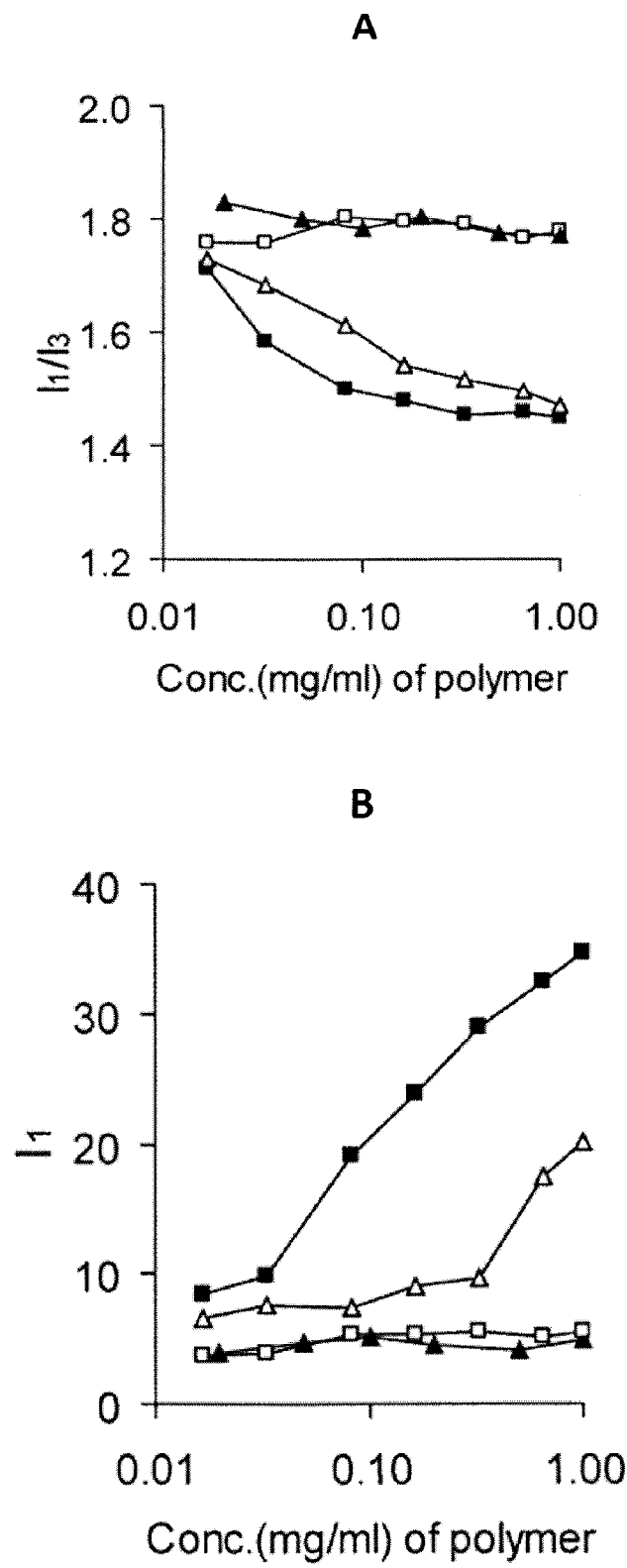

FIG. 10A provides a graph of the variation of the $I_1/I_3$ ratio ($I_{373\ nm}/I_{383\ nm}$) and FIG. 10B provides a graph of the normalized emission fluorescence intensity at 373 nm ($I_1$) for various PGA-based polypeptides and cross-linked micelles as a function of polymer concentration at 25° C. and pH 7.0. (▲) PEO-b-PGA, (□) PEO-b-PPGA25, (Δ) PEO-b-PPGA50 and (■) cl-PEO-b-PPGA50. Concentration of pyrene is $6 \times 10^{-7}$ M.

FIG. 11A provides a graph of the normalized steady-state emission spectra and FIG. 11B provides a graph of the lifetime measurement of C153 in aqueous solutions of various poly(L-glutamic acid) and cross-linked micelles. (1) phosphate buffer (10 mM, pH 7.0) (2) PEO-b-PGA, (3)

PEO-b-PPGA25, (4) PEO-b-PPGA50, (5) cl-PEO-b-PPGA50, and (6) instrumental response. Concentration of polymers is 1 mg/ml at pH 7.0.

Figure 12:
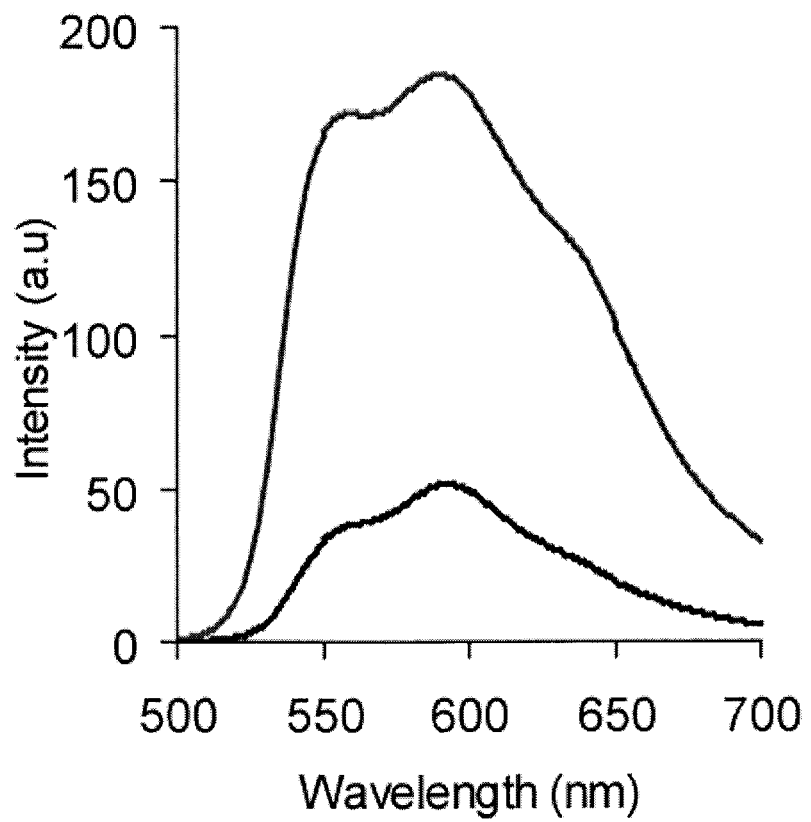

FIG. 12 provides a graph of the fluorescence quenching effect of DOX in DOX-loaded cl-micelles.

Figure 13:
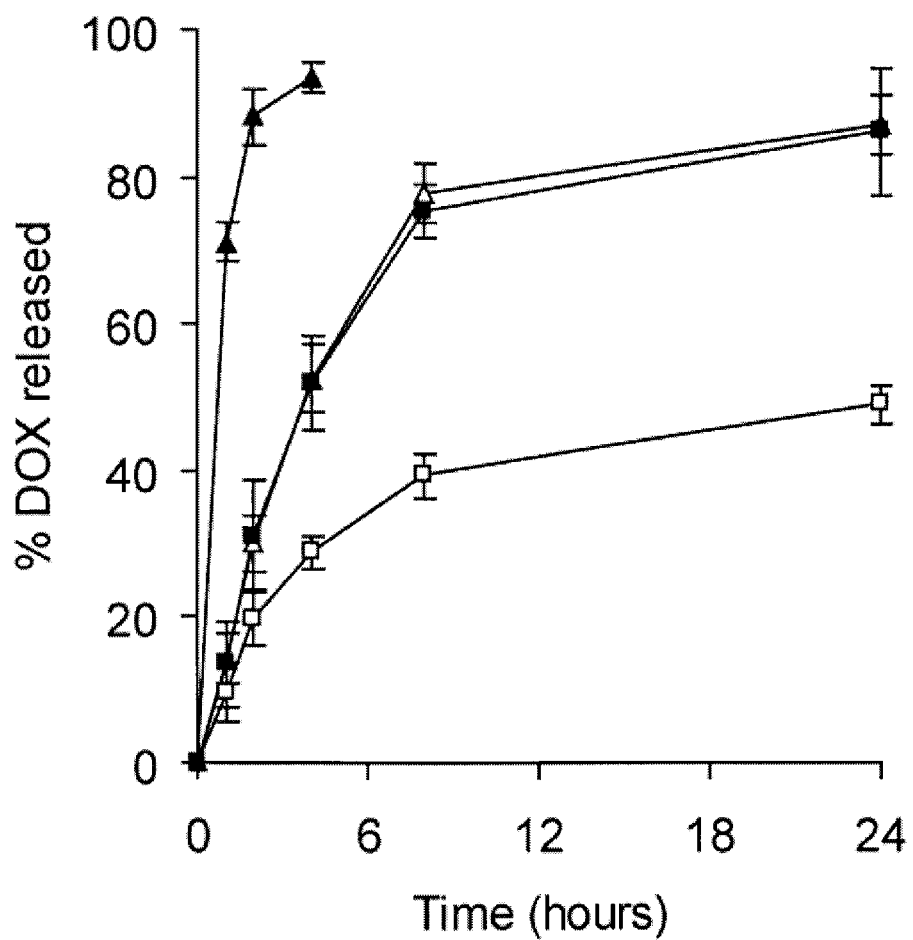

FIG. 13 provides a graph of the release profiles of DOX from cl-PEO-b-PPGA micelles in PBS buffer (0.14 M NaCl, pH 7.4) at 37° C. (□) cl-PEO-b-PPGA, (■) cl-PEO-b-PGA, (Δ) PEO-b-PPGA and (▲) free DOX. The loading amount of DOX for each sample is 200 µg. The data expressed average and standard deviation of three independent measurements.

Figure 14:
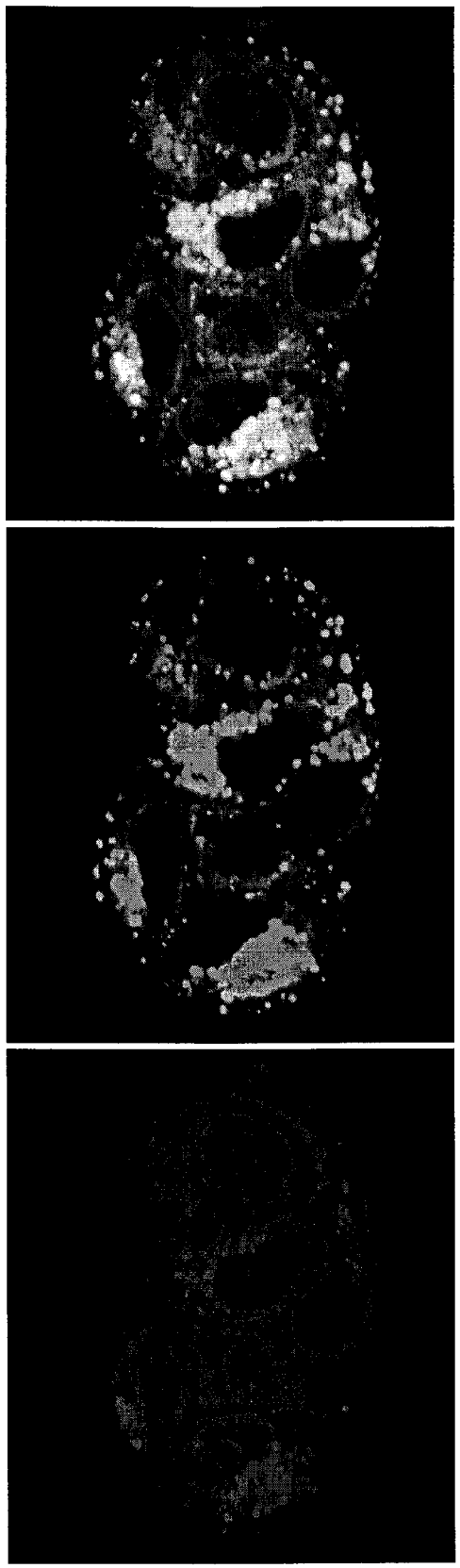

FIG. 14 provides images of the cellular localization of DOX-loaded cl-PEO-b-PPGA50 micelles in MCF-7 cells. MCF-7 cells were exposed for 45 minutes at 37° C. to DOX-loaded cl-PEO-b-PPGA50 micelles (left) and Lysotracker® (middle) for 10 minutes. Live cell imagings of MCF-7 show significant co-localization (right) of cl-PEO-b-PPGA50 with the lysosomes.

DETAILED DESCRIPTION OF THE INVENTION

Novel biodegradable cross-linked (cl) micelles based on polypeptide block copolymers were prepared and characterized for drug delivery (e.g., the delivery of anticancer drugs). A poly(ethylene oxide)-b-poly(L-glutamic acid) with the hydrophobic amino acid phenylalanine (Phe) (PEO-b-PPGA) was synthesized. The modification of Phe on the backbone of PGA make the polypeptides self-assemble with $Ca^{2+}$, due to increased packing and stability of the hydrophobic cores. The complexation behavior of PEO-b-PGA complexes with $Ca^{2+}$ was dependent on the degree of hydrophobic Phe on the PGA segments. Self-assembly behavior of PEO-b-PPGA with divalent metal cation ($Ca^{2+}$) was utilized as templates for synthesis of polypeptide micelles. The resulting polypeptide micelles showed pH-dependent swelling behavior with small particle size (ca. 70 nm at pH 7.0), which was influenced by the ionization state of the carboxylic groups and secondary structure of the PGA chains of the micelles. The cross-linked ionic cores with hydrophobic moiety allowed for encapsulation of doxorubicin (DOX) with high loading capacity (ca. 30 w/w %) and showed sustained release of DOX. In addition, DOX-loaded cl-micelles internalized into the lysosomes and the released DOX accumulated in the nucleus. Therefore, the biodegradable polypeptide micelles with the cross-linked ionic cores of the instant invention can immobilize and deliver bioactive agents (e.g., pharmaceutically-active agent) such as anticancer drugs (e.g., DOX). In a particular embodiment, the micelles further comprise (e.g., via physical or chemical coupling) at least one targeting molecules for site-specific (e.g., cell or tissue type specific) delivery and recognition in the body. These novel biodegradable polypeptide micelles can be used for pharmaceutical and biomedical applications, such as drug delivery, diagnostics, imaging, and the like.

In accordance with the instant invention, compositions and methods for administering an effective amount of at least one biological agent (e.g., a therapeutic agent, especially an anticancer drug) using delivery vehicles of polymer micelles with at least one hydrophobic moiety in the cross-linked ionic core are provided. The invention encompasses methods for delivering at least one bioactive agent or combination of biological agents to a cell, tissue (including, without limitation, cancerous tissue and/or tumors), or organs, comprising contacting the cell, tissue, or organ, in vivo or in vitro, with a composition comprising the biological agent(s) in micelles of the instant invention. In a particular embodiment, these methods and compositions allow one or more agents to be simultaneously delivered to the disease site. The contact may be for a period of time sufficient to introduce the agents to the locus of the cell, tissue, or organ.

The compositions and methods of the instant invention allow for two or more agents (e.g., bioactive agent, imaging agents, therapeutic agent, etc.) to be maintained at the disease site in a coordinated fashion (e.g., delivery of synergistic compounds). In a particular embodiment, the compositions and methods of the instant invention are used for the effective combination delivery of at least one therapeutic agent and at least one diagnostic and/or imaging agent. The encapsulated biological agents may be charged, nonpolar, or hydrophobic compounds. The agents can be organic or inorganic. The agents may be stabilized within the core by non-covalent electrostatic and/or hydrophobic and/or nonpolar interactions. The ionic character of the core allows for the encapsulation of various charged molecules including, without limitation, both low molecular mass and biological agents such as small molecules, oligo- and poly-saccharides, polypeptides and proteins, nucleic acid molecules (e.g., polynucleotides, siRNA, antisnense molecules, etc.), and the like. Insoluble and hydrophobic agents can be immobilized through the interactions with hydrophobic groups in the core. The complexed micelles of the instant invention remain stable in aqueous dispersion due to the effect of hydrophilic exterior shell chains. The simultaneous delivery of multiple agents can provide a synergistic effect so that a lower effective does is required for a suitable therapeutic benefit. In a particular embodiment, the micelle comprises at least one charged compound and at least one nonpolar hydrophobic compound.

In accordance with another aspect of the instant invention, methods are provided for synthesizing the micelles of the instant invention. In a particular embodiment, the method comprises at least partially hydrophobizing the ionically-charged polymeric segment of at least one block polymer having at least one ionically-charged polymeric segment and at least one non ionically-charged polymeric segment (hydrophilic); neutralizing the ionically-charged polymeric segments with moieties of opposite charge (e.g., a metal ion (e.g., $Ca^{+2}$) or a surfactant) under conditions that allow for self-assembly of polymer micelles; cross-linking the neutralized ionically-charged polymer segments with a cross-linking agent; and removing the moieties of opposite charge and unreacted cross-linking agent.

The instant invention also encompasses compositions comprising at least one polymer micelles with hydrophobic moieties in the cross-linked ionic core and at least one biological agent such as therapeutic, diagnostic, and/or imaging agents. The compositions may further comprise at least one pharmaceutically acceptable carrier. The compositions of this invention are useful in pharmaceutics and biopharmaceutics, diagnostics and imaging, immunology, and other areas, where the properties of biological agents exhibited during interaction with a living organism or cells can be improved by formulation.

According to another aspect of the instant invention, methods for treating, inhibiting, and/or preventing a disease or disorder in a subject are provided. In a particular embodiment, the disease is cancer. The methods may comprise the administration of at least one micelle of the instant invention comprising at least one biological agent. The micelles may be in a composition further comprising at least one pharmaceutically acceptable carrier. In a particular embodiment, the biological agent is a chemotherapeutic agent. In a particular embodiment, the administered micelles comprise at least two biological agents, particularly at least two therapeutic agents (e.g., chemotherapeutic agents that function synergistically together).

The micelles of the instant invention comprise at least one block copolymer. The block copolymer comprises at least one ionically charged polymeric segment and at least one non-ionically charged polymeric segment (e.g., hydrophilic segment). In a particular embodiment, the block copolymer has the structure A-B or B-A. The block copolymer may also comprise more than 2 blocks. For example, the block copolymer may have the structure A-B-A, wherein B is an ionically charged polymeric segment. In a particular embodiment, the segments of the block copolymer comprise about 20 to about 300 repeating units, about 50 to about 250 repeating units, about 75 to about 200 repeating units, or about 100 to about 175 repeating units.

The ionically charged polymeric segment may be cationic or anionic. The ionically charged polymeric segment may be selected from, without limitation, polymethylacrylic acid and its salts, polyacrylic acid and its salts, copolymers of acrylic acid and its salts, poly(phosphate), polyamino acids (e.g., polyglutamic acid, polyaspartic acid), polymalic acid, polylactic acid, homopolymers or copolymers or salts thereof of aspartic acid, 1,4-phenylenediacrylic acid, ciraconic acid, citraconic anhydride, trans-cinnamic acid, 4-hydroxy-3-methoxy cinnamic acid, p-hydroxy cinnamic acid, trans glutaconic acid, glutamic acid, itaconic acid, linoleic acid, linlenic acid, methacrylic acid, maleic acid, trans-β3-hydromuconic acid, trans-trans muconic acid, oleic acid, vinylsulfonic acid, vinyl phosphonic acid, vinyl benzoic acid, and vinyl glycolic acid and the like and carboxylated dextran, sulfonated dextran, heparin and the like. Examples of polycationic segments include but are not limited to polymers and copolymers and their salts comprising units deriving from one or several monomers including, without limitation: primary, secondary and tertiary amines, each of which can be partially or completely quaternized forming quaternary ammonium salts. Examples of these monomers include, without limitation, cationic aminoacids (e.g., lysine, arginine, histidine), alkyleneimines (e.g., ethyleneimine, propyleneimine, butileneimine, pentyleneimine, hexyleneimine, and the like), spermine, vinyl monomers (e.g., vinylcaprolactam, vinylpyridine, and the like), acrylates and methacrylates (e.g., N,N-dimethylaminoethyl acrylate, N,N-dimethylaminoethyl methacrylate, N,N-diethylaminoethyl acrylate, N,N-diethylaminoethyl methacrylate, t-butylaminoethyl methacrylate, acryloxyethyltrimethyl ammonium halide, acryloxyethyl-dimethylbenzyl ammonium halide, methacrylamidopropyltrimethyl ammonium halide and the like), allyl monomers (e.g., dimethyl diallyl ammoniam chloride), aliphatic, heterocyclic or aromatic ionenes. Examples of non-ionically charged water soluble polymeric segments include, without limitation, polyetherglycols, poly(ethylene oxide), copolymers of ethylene oxide and propylene oxide, polysaccharides, polyvinyl alcohol, polyvinyl pyrrolidone, polyvinyltriazole, N-oxide of polyvinylpyridine, N-(2-hydroxypropyl)methacrylamide (HPMA), poly-ortho esters, polyglycerols, polyacrylamide, polyoxazolines, polyacroylmorpholine, and copolymers or derivatives thereof.

The ionically charged segment of the polymers of the instant invention comprises at least one hydrophobic moiety. The hydrophobization of the ionically charged segment yields an amphiphilic block copolymer with the non-ionically charged water soluble polymeric segment. In a particular embodiment, the degree of grafting of the hydrophobic moiety is at least about 20%, at least about 25%, at least about 30%, at least about 35%, at least about 40% or more. The hydrophobic moiety can be coupled to the ionically charged segment by any means including, for example, linking with functional groups of the ionically charged segment. The hydrophobic moiety may be linked directly to the ionically charged segment or via a linker. Generally, the linker is a chemical moiety comprising a covalent bond or a chain of atoms that covalently attaches the ligand to the surfactant. The linker can be linked to any synthetically feasible position of the hydrophobic moiety and the ionically charged segment. The linker may be degradable (e.g., substantially cleaved under physiological environments or conditions) or non-degradable. The linker may be a covalent bond or any other chemical structure which cannot be substantially cleaved or cleaved at all under physiological environments or conditions.

In a particular embodiment, the hydrophobic moiety is a compound with a relatively low molecular weight (e.g., less than 4,000, less than 2,000, or less than 1 kDa or 800 Da). In a particular embodiment, the hydrophobic moiety is a lipid, fatty acid (saturated or unsaturated), steroid, or cholesterol. In a particular embodiment, the hydrophobic moiety is a hydrophobic amino acid such as Val, Ile, Leu, Ala, Met, Phe, Trp, and Tyr—particularly phenylalanine. In a particular embodiment, the hydrophobic moiety comprises at least one linear, branched or cyclic alkyl group, alkenyl group, and/or at least one aryl group.

The polymer micelles of the instant invention may self-assemble by neutralizing the ionically-charged polymeric segments with moieties of opposite charge. The neutralization of the charge allows for the creation of a hydrophobic core and hydrophilic shell formation of a micelle. In a particular embodiment, the neutralizing agent binds well and forms a complex with the polyionic segment, but is also easily removed (e.g., by dialysis, chromatography, ultrafiltration, centrifugation, or other means known in the art) and compatible with micelle chemistry. In a particular embodiment, the neutralizing agent is an ion or salt (e.g., metal ion) or a surfactant. The ion may be a mono-, di-, tri-, or multivalent ion. Examples of cations include, for example, $Ca^{+2}$, $Mg^{+2}$, $Ba^{+2}$ and $Sr^{+2}$ or multivalent cations such as spermine, spermidine, and the like. Examples of anions include, without limitation, $Cl^-$ and $Br^-$. Surfactants that may be used as neutralizing agents include, without limitation single-, double- or triple-tailed surfactants. Examples of cationic surfactants and anionic surfactants are provided in U.S. Pat. No. 7,332,527.

As stated hereinabove, the cores of the micelles of the instant invention are cross-linked. In a particular embodiment, the degree of cross-linking is at least about 5%, at least about 10%, at least about 15%, at least about 20%, at least about 25%, at least about 30%, at least about 50%, or more. The cross-linking of the inner core prevents the micelle from degradation upon dilution. Further, the biological agents contained within the core are protected from premature release and degradation. The hydrophilic outer shell of the micelles provides increased solubility and reduces unwanted interactions with blood plasma components. Additionally, the nanoscale size of the micelles of the instant invention avoids renal excretion but allows the micelles to invade sites, such as those with enhanced vascular permeability such as tumor tissue.

The term "cross-linker" refers to a molecule capable of forming a covalent linkage between compounds (e.g., polymers) or between two different regions of the same compound (e.g., polymer). In a particular embodiment, the cross-linker forms covalent linkages among the ionically charged polymeric segment, is compatible with micelle chemistry, and excess cross-linker is also easily removed (e.g., by dialysis or other means known in the art). Cross-linkers are well known in the art. In a particular embodiment, the cross-linker is a titrimetric cross-linking reagent. The cross-linker may be a bifunctional, trifunctional, or multifunctional cross-linking reagent. Examples of cross-linkers are provided in U.S. Pat. No. 7,332,527. Cross-linking of the ionic core domain can be achieved by a variety of means including, without limitation, condensation reactions, addition reactions, or chain polymerization reactions (e.g., cationic chain polymerization, anionic chain polymerization, radical chain polymerization, and ring opening chain polymerization). Cross-linking may be achieved, without limitation, photochemically, spontaneously, by addition of a chain polymerization initiator, or by addition of titrimetric cross-linking reagents. Titrimetric cross-linkers can have a variety of functional groups useful in reacting with functionalities on the amphiphilic copolymers such as, without limitation, nucleophilic groups, electrophilic groups, and groups which participate in pericyclic reactions. Titrimetric cross-linkers include, without limitation, multifunctional compounds such as polyols, polyamines, polyethyleneglycol multiarm stars, polycarboxylic acids, polycarboxylic acid halides, polyisocyanates, polymeric aromatic isocyanates, polyalkylhalides, polysulfonates, polysulfates, polyphosphonates, polyphosphates, alkyldiamines, alkanediols, ethanolamine, poly(oxyethylene), amino-substituted poly(oxyethylene), diamino-substituted poly(oxyethylene), poly(ethyleneimine), polyamino-substituted poly(oxyethylene), amino-substituted alcohols, substituted dendrimers, and substituted hyperbranched polymers.

The cross-linked micelles of the instant invention are stable and control diffusion of the encapsulated compound(s). The rate of diffusion can be controlled the properties of cross-linked core of the micelle by, for example, the nature of cross-linking agent, the degree of cross-linking, and/or the composition of polyion-metal complex. Of course, the micelle must also release the entrapped compound(s) at the target site. In a particular embodiment, the cross-linker is reversible and/or biodegradable. In a particular embodiment, the cross-linker comprises a bond which may be cleaved in response to chemical stimuli (e.g., a disulfide bond that is degraded in the presence of intracellular glutathione). The cross-linkers may also be sensitive to pH (e.g., low pH).

In a particular embodiment, the micelles are conjugated to at least one targeting ligand, particularly on the outer portion of the shell. A targeting ligand is a compound that will specifically bind to a specific type of tissue or cell type. In a particular embodiment, the targeting ligand is a ligand for a cell surface marker/receptor. The targeting ligand may be an antibody or fragment thereof immunologically specific for a cell surface marker (e.g., protein or carbohydrate) preferentially or exclusively expressed on the targeted tissue or cell type. The targeting ligand can be coupled to the micelles by any means including, for example, linking with functional groups of the non-ionic polymeric shell segments. The targeting ligand may be linked directly to the micelle or via a linker. Generally, the linker is a chemical moiety comprising a covalent bond or a chain of atoms that covalently attaches the ligand to the micelle. The linker can be linked to any synthetically feasible position of the ligand and the non-ionic polymeric shell segments. Exemplary linkers may comprise at least one optionally substituted; saturated or unsaturated; linear, branched or cyclic alkyl group or an optionally substituted aryl group. The linker may also be a polypeptide (e.g., from about 1 to about 10 amino acids, particularly about 1 to about 5). The linker may be degradable or non-degradable. The linker may be a covalent bond or any other chemical structure which cannot be substantially cleaved or cleaved at all under physiological environments or conditions.

As stated hereinabove, the micelles of the instant invention can encapsulate at least one compound. The compound(s) can be, without limitation, a biological agent, imaging agent, or therapeutic agent. The biological agents that can be used in the present invention include, without limitation, inorganic and organic compounds, including drugs that act on cancerous tissues, tumors, the peripheral nerves, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, reproductive system, skeletal system, autatory of autocoid systems, alimentary and excretory systems, inhibitory of autocoids and histamine systems. Examples of therapeutic agents include, without limitation, anticonvulsants, analgesics, anti-inflammatories, calcium antagonists, anesthetics, antimicrobials, antimalarials, antiparasitics, antihypertensives, antihistamines, antipyretics, alpha-andrenergic agonist, alpha-blockers, anti-tumor compounds, biocides, bactericides, bronchial dilators, beta-andrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, opthalmics, psychic energizers, parasympathomimetics, saccharides, sedatives, sympathomimetics, tranquilizers, urinary tract drugs, vaginal drugs, vitamins, nonsteroidal anti-inflammatory drugs, angiotensin converting enzymes, polypeptides, proteins, and the like.

The compounds encapsulated by the micelles of the instant invention include, without limitation, bioactive agents, therapeutics, diagnostics, nucleic acid molecules, DNA (e.g., oligonucleotides and plasmids), RNA (e.g., RNAi), proteins, polypeptides, polysaccharides, small molecules, and the like. As used herein, the term "bioactive agent" also includes compounds to be screened as potential leads in the development of drugs or plant protecting agents. Bioactive agent and therapeutic agents include, without limitation, polypeptides, peptides, glycoproteins, nucleic acids, synthetic and natural drugs, peptoides, polyenes, macrocyles, glycosides, terpenes, terpenoids, aliphatic and aromatic compounds, small molecules, and their derivatives and salts. In a particular embodiment, the therapeutic agent is a chemical compound such as a synthetic and natural drug.

Chemotherapeutic agents are compounds that exhibit anticancer activity and/or are detrimental to a cell (e.g., a toxin). Suitable chemotherapeutic agents include, but are not limited to: toxins (e.g., saporin, ricin, abrin, ethidium bromide, diptheria toxin, *Pseudomonas* exotoxin); alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, vinblastine, and paclitaxel (Taxol®)); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); HSP90 inhibitors (e.g., 17-AAG); and antihormonal antigens (e.g., tamoxifen, antiandrogen agents such as flutamide; and antiadrenal agents such as mitotane and aminoglutethimide). In a particular embodiment, the chemotherapeutic agent is doxorubicin or doxorubicin with a synergistic chemotherapeutic agent such as paclitaxel or 17-AAG.

When employed for detecting and/or imaging cells (e.g., cancer cells), the micelles of the invention can be encapsulate radioisotopes, detectable labels, imaging agent, and/or contrast agent. Detectable labels, imaging agents, or contrast agents include, without limitation, paramagnetic or superparamagnetic ions for detection by MRI imaging, isotopes (e.g., radioisotopes (e.g., $^3$H (tritium) and $^{14}$C) or stable isotopes (e.g., $^2$H (deuterium), $^{11}$C, $^{13}$C, $^{17}$O and $^{18}$O), optical agents, and fluorescence agents. Paramagnetic ions include, without limitation, Gd(III), Eu(III), Dy(III), Pr(III), Pa(IV), Mn(II), Cr(III), Co(III), Fe(III), Cu(II), Ni(II), Ti(III), and V(IV). Fluorescent agents include, without limitation, fluorescein and rhodamine and their derivatives. Optical agents include, without limitation, derivatives of phorphyrins, anthraquinones, anthrapyrazoles, perylenequinones, xanthenes, cyanines, acridines, phenoxazines and phenothiazines.

The instant invention encompasses compositions comprising at least one micelle of the instant invention and at least one pharmaceutically acceptable carrier. As stated hereinabove, the micelle may comprise more than one bioactive agent or therapeutic agent. In a particular embodiment, the composition comprises a first micelle comprising a first therapeutic agent(s) and a second micelle comprising a second therapeutic agent(s), wherein the first and second therapeutic agent(s) are different. The compositions of the instant invention may further comprise other therapeutic agents (e.g., other chemotherapeutic agents).

The present invention also encompasses methods for preventing, inhibiting, and/or treating a disease or disorder, particularly cancer. The pharmaceutical compositions of the instant invention can be administered to an animal, in particular a mammal, more particularly a human, in order to treat/inhibit/prevent the disease or disorder. The pharmaceutical compositions of the instant invention may also comprise at least one other bioactive agent, particularly at least one other therapeutic agent. The additional agent may also be administered in separate composition from the micelles of the instant invention. The compositions may be administered at the same time or at different times (e.g., sequentially). When the disease is cancer, the compositions of the instant invention may also be administered with chemoradiation (e.g., sequentially).

The dosage ranges for the administration of the compositions of the invention are those large enough to produce the desired effect. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications.

The micelles described herein will generally be administered to a patient as a pharmaceutical preparation. The term "patient" as used herein refers to human or animal subjects. These micelles may be employed therapeutically, under the guidance of a physician. While the therapeutic agents are exemplified herein, any bioactive agent may be administered to a patient, e.g., a diagnostic or imaging agent.

The compositions comprising the micelles of the instant invention may be conveniently formulated for administration with any pharmaceutically acceptable carrier(s). For example, the micelles may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the micelles in the chosen medium may be varied and the medium may be chosen based on the desired route of administration of the pharmaceutical preparation. Except insofar as any conventional media or agent is incompatible with the micelles to be administered, its use in the pharmaceutical preparation is contemplated.

The dose and dosage regimen of micelles according to the invention that are suitable for administration to a particular patient may be determined by a physician considering the patient's age, sex, weight, general medical condition, and the specific condition for which the micelles are being administered and the severity thereof. The physician may also take into account the route of administration, the pharmaceutical carrier, and the biological activity of the micelle.

Selection of a suitable pharmaceutical preparation will also depend upon the mode of administration chosen. For example, the micelles of the invention may be administered by direct injection (e.g., intratumor or to the surrounding area) or intravenously. In this instance, a pharmaceutical preparation comprises the micelle dispersed in a medium that is compatible with the site of injection.

Micelles of the instant invention may be administered by any method. For example, the micelles of the instant invention can be administered, without limitation parenterally, subcutaneously, orally, topically, pulmonarily, rectally, vaginally, intravenously, intraperitoneally, intrathecally, intracerbrally, epidurally, intramuscularly, intradermally, or intracarotidly. In a particular embodiment, the micelles are administered intravenously or intraperitoneally. Pharmaceutical preparations for injection are known in the art. If injection is selected as a method for administering the micelle, steps must be taken to ensure that sufficient amounts of the molecules reach their target cells to exert a biological effect. Dosage forms for oral administration include, without limitation, tablets (e.g., coated and uncoated, chewable), gelatin capsules (e.g., soft or hard), lozenges, troches, solutions, emulsions, suspensions, syrups, elixirs, powders/granules (e.g., reconstitutable or dispersible) gums, and effervescent tablets. Dosage forms for parenteral administration include, without limitation, solutions, emulsions, suspensions, dispersions and powders/granules for reconstitution. Dosage forms for topical administration include, without limitation, creams, gels, ointments, salves, patches and transdermal delivery systems.

Pharmaceutical compositions containing a micelle of the present invention as the active ingredient in intimate admixture with a pharmaceutically acceptable carrier can be prepared according to conventional pharmaceutical compounding techniques. The carrier may take a wide variety of forms depending on the form of preparation desired for administration, e.g., intravenous, oral, direct injection, intracranial, and intravitreal.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of micelles may be determined by evaluating the toxicity of the molecules or cells in animal models. Various concentrations of micelles in pharmaceutical preparations may be administered to mice, and the minimal and maximal dosages may be determined based on the beneficial results and side effects observed as a result of the treatment. Appropriate dosage unit may also be determined by assessing the efficacy of the micelle treatment in combination with other standard drugs. The dosage units of micelle may be determined individually or in combination with each treatment according to the effect detected.

The pharmaceutical preparation comprising the micelles may be administered at appropriate intervals, for example, at least twice a day or more until the pathological symptoms are reduced or alleviated, after which the dosage may be reduced to a maintenance level. The appropriate interval in a particular case would normally depend on the condition of the patient.

The instant invention encompasses methods of treating a disease/disorder comprising administering to a subject in need thereof a composition comprising a micelle of the instant invention and, particularly, at least one pharmaceutically acceptable carrier. Other methods of treating the disease or disorder may be combined with the methods of the instant invention may be co-administered with the compositions of the instant invention. The instant invention also encompasses ex vivo methods of treatment. The instant also encompasses delivering the micelle of the instant invention to a cell in vitro (e.g., in culture). The micelle may be delivered to the cell in at least one carrier.

Definitions

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions may be employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "prevent" refers to the prophylactic treatment of a subject who is at risk of developing a condition (e.g., cancer) resulting in a decrease in the probability that the subject will develop the condition.

As used herein, the term "subject" refers to an animal, particularly a mammal, particularly a human.

A "therapeutically effective amount" of a compound or a pharmaceutical composition refers to an amount effective to prevent, inhibit, treat, or lessen the symptoms of a particular disorder or disease. The treatment of cancer herein may refer to curing, relieving, and/or preventing the cancer, the symptom(s) of it, or the predisposition towards it.

As used herein, the term "therapeutic agent" refers to a chemical compound or biological molecule including, without limitation, nucleic acids, peptides, proteins, and antibodies that can be used to treat a condition, disease, or disorder or reduce the symptoms of the condition, disease, or disorder.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, or nucleic acids, though they may be amino acids or dipeptides.

As used herein, the term "amphiphilic" means the ability to dissolve in both water and lipids/apolar environments. Typically, an amphiphilic compound comprises a hydrophilic portion and a hydrophobic portion. "Hydrophobic" designates a preference for apolar environments (e.g., a hydrophobic substance or moiety is more readily dissolved in or wetted by non-polar solvents, such as hydrocarbons, than by water). As used herein, the term "hydrophilic" means the ability to dissolve in water.

As used herein, the term "polymer" denotes molecules formed from the chemical union of two or more repeating units or monomers. The term "block copolymer" most simply refers to conjugates of at least two different polymer segments, wherein each polymer segment comprises two or more adjacent units of the same kind.

An "antibody" or "antibody molecule" is any immunoglobulin, including antibodies and fragments thereof (e.g., scFv), that binds to a specific antigen. As used herein, antibody or antibody molecule contemplates intact immunoglobulin molecules, immunologically active portions of an immunoglobulin molecule, and fusions of immunologically active portions of an immunoglobulin molecule.

As used herein, the term "immunologically specific" refers to proteins/polypeptides, particularly antibodies, that bind to one or more epitopes of a protein or compound of interest, but which do not substantially recognize and bind other molecules in a sample containing a mixed population of antigenic biological molecules.

The term "alkyl," as employed herein, includes straight, branched, and cyclic chain hydrocarbons containing 1 to about 20 carbons or 1 to about 10 carbons in the normal chain. The hydrocarbon chain of the alkyl groups may be interrupted with one or more oxygen, nitrogen, or sulfur. Examples of suitable alkyl groups include methyl, ethyl, propyl, isopropyl, butyl, t-butyl, isobutyl, pentyl, hexyl, isohexyl, heptyl, 4,4 dimethylpentyl, octyl, 2,2,4 trimethylpentyl, nonyl, decyl, the various branched chain isomers thereof, and the like. Each alkyl group may, optionally, be substituted, preferably with 1 to 4 substituents. The term "lower alkyl" refers to an alkyl which contains 1 to 3 carbons in the hydrocarbon chain. The term "cyclic alkyl" or "cycloalkyl," as employed herein, includes cyclic hydrocarbon groups containing 1 to 3 rings which may be fused or unfused. Cycloalkyl groups may contain a total of 3 to 20 carbons forming the ring(s), particularly 6 to 10 carbons forming the ring(s). Optionally, one of the rings may be an aromatic ring as described below for aryl. The cycloalkyl groups may also, optionally, contain substituted rings that includes at least one (e.g., from 1 to about 4) sulfur, oxygen, or nitrogen heteroatom ring members. Each cycloalkyl group may be, optionally, substituted, with 1 to about 4 substituents. Alkyl substituents include, without limitation, alkyl, alkenyl, halo (such as F, Cl, Br, I), haloalkyl (e.g., $CCl_3$ or $CF_3$), alkoxyl, alkylthio, hydroxy, methoxy, carboxyl, oxo, epoxy, alkyloxycarbonyl, alkylcarbonyloxy, amino, carbamoyl (e.g., $NH_2C(=O)$— or $NHRC(=O)$—, wherein R is an alkyl), urea (—$NHCONH_2$), alkylurea, aryl, ether, ester, thioester, nitrile, nitro, amide, carbonyl, carboxylate and thiol. In a particular embodiment, the substituent is hydrophobic such as an alkyl or aryl.

"Alkenyl" refers to an unsubstituted or substituted hydrocarbon moiety comprising one or more carbon to carbon double bonds (i.e., the alkenyl group is unsaturated) and containing from 1 to about 20 carbon atoms or from 1 to about 10 carbon atoms, which may be a straight, branched, or cyclic hydrocarbon group. The hydrocarbon chain of the alkenyl groups may be interrupted with one or more oxygen, nitrogen, or sulfur. When substituted, alkenyl groups may be substituted at any available point of attachment. Exemplary substituents are described above for alkyl groups.

The term "aryl," as employed herein, refers to monocyclic and bicyclic aromatic groups containing 6 to 10 carbons in the ring portion. Examples of aryl groups include, without limitation, phenyl, naphthyl, such as 1-naphthyl and 2-naphthyl, indolyl, and pyridyl, such as 3-pyridyl and 4-pyridyl. Aryl groups may be optionally substituted through available carbon atoms, preferably with 1 to about 4 groups. Exemplary substituents are described above for alkyl groups. The aryl groups may be interrupted with one or more oxygen, nitrogen, or sulfur heteroatom ring members (e.g., a heteroaryl).

The following examples provide illustrative methods of practicing the instant invention and are not intended to limit the scope of the invention in any way.

EXAMPLE 1

Recently, nanofabrication of polymer micelles has been considerably advanced by utilizing block copolymers containing ionic and nonionic blocks ("block ionomers"). Such block copolymers can react with oppositely charged species through electrostatic interaction, resulting in block ionomer complexes (BIC).

Among block copolymers with an amphiphilic character, poly(amino acids)-based block copolymers are particularly interesting because of their biocompatibility, non-toxicity, biofunctionality and biodegradability (Lavasanifar et al. (2002) Adv. Drug Deliv. Rev., 54:169-190; Carlsen et al. (2009) Curr. Opin. Coll. Interface Sci., 14:329-339; Li et al. (2002) Adv. Drug Deliv. Rev., 54:695-713). For instance, several micellar formulations have been developed which consisted of PEG as a hydrophilic non-ionic block and poly(amino acids) as an ionic block for delivery of anti-cancer drugs and other macromolecules (Matsumura, Y. (2008) Adv. Drug Deliv. Rev., 60:899-914; Hamaguchi et al. (2005) Br. J. Cancer, 92:1240-1246; Nishiyama et al. (2003) Cancer Res., 63:8977-8983; Kakizawa et al. (2002) Adv. Drug Deliv. Rev., 21:203-222). Self-assembled polypeptide vesicles have also been demonstrated that were sensitive to environmental stimuli by the ordered conformations assembly of the polypeptide segment with stable helical conformations (Bellomo et al. (2004) Nat. Mater., 3:244-248; Holowka et al. (2005) J. Am. Chem. Soc., 127:12423-12428; Holowka et al. (2007) Nat. Mater., 6:52-57; Checot et al. (2002) Angew Chem. Int. Ed. Engl., 41:1339-1343; Upadhyay et al. (2009) Biomacromolecules 10:2802-2808; Rodriguez-Hernandez et al. (2005) J. Am. Chem. Soc., 127:2026-2027). Functional groups such as amines and carboxylic groups in the core-forming polypeptides could be utilized for incorporating therapeutic molecules into the core of micelle. Therefore, polypeptides-based nanocarriers are useful as ideal drug delivery vehicles for the various charged therapeutic molecules, including proteins and nucleic acids.

Template-assisted synthetic procedures have been proposed for preparation of polymer micelles with cross-linked ionic cores (Bronich et al. (2005) J. Am. Chem. Soc., 127:8236-8237; Bronich et al. (2006) J. Drug Target, 14:357-366; Bontha et al. (2006) J. Control Release, 114: 163-174; Kim et al. (2009) J. Control Release, 138:197-204). In order to provide high stability without fast disintegration of polymer micelles in biological surroundings, the ionic cores of polymer micelles were cross-linked using BIC between polyion charge segments of block copolymer with $Ca^{2+}$ ions, surrounded by PEO shell. Cross-linked polymer micelles represented pH- and ionic strength-responsive soft hydrogel-like behavior.

Herein, this approach is demonstrated for development of drug delivery vehicles based on polypeptide copolymers for anti-cancer drug DOX which is positively charged at physiological conditions. First, the soft nanomaterials were developed by using self-assembly behavior of the phenylalanine-modified poly(ethylene oxide)-b-poly(L-glutamic acid) (PEO-b-PPGA) with multivalent $Ca^{2+}$ ions. Poly(L-glutamic acid) (PGA) is biodegradable in vivo and has been used for potential anti-cancer drug carriers (Li et al. (2002) Adv. Drug Deliv. Rev., 54:695-713). By introducing of hydrophobic amino acid to core-forming segments, PGA, stable BIC micelles were formed. Second, the physicochemical properties such as swelling behavior, pH-dependent conformation transition of polypeptide and hydrophobicity of cores were evaluated. Further, loading capacity and release behavior of DOX from the micelles were evaluated. To evaluate the biological activity, the cellular uptake and in vitro cytotoxicity of DOX-loaded micelles were also performed in MCF-7 breast cancer cells. All together, novel degradable polypeptide micelles with hydrophobized ionic cores are shown to be effective carriers for the delivery of biological agents such as anti-cancer drugs.

Materials and Methods

Materials

Poly(ethylene oxide)-b-Poly(L-glutamic acid) (PEO-b-PGA) diblock copolymer ($M_w/M_n$=1.38, MW 27,500) was purchased from Alamanda Polymers, Inc. (Madison, Ala., USA). The block lengths were 114 and 150 repeating units for PEO and PGA, respectively. Doxorubicin hydrochloride was obtained from Dong-A Pharmaceutical Co., South Korea. L-phenylalanine methyl ester HCl (Phe), calcium chloride, cystamine (Cys), 1-(3-dimethylaminopropyl)-3-ethylcarbodiimide hydrochloride (EDC) and coumarin 153 (C153) were obtained from Sigma-Aldrich (St. Louis, Mo.). Lysotracker™ (green), fetal bovine serum (FBS) (both dialyzed and heat inactivated) and Dulbecco's Modified Eagle's Medium (DMEM), were purchased from Invitrogen Inc. (Carlsbad, Calif.). Bovine serum albumin (BSA) and NUNC™ chambered glass coverslips for live cell imaging was purchased from (Fisher Scientific, Waltham, Mass.). MTT reagent (3-(4,5-Dimethylthiazol-2-yl)-2,5-diphenyltetrazolium bromide) was purchased from Research Products International (Prospect, Ill.). All other chemicals were of reagent grade and used without further purification.

Synthesis of Hydrophobized PEO-b-PGA

PEO-b-PGA (100 mg, 0.545 mmol as carboxylate groups) was hydrophobically modified by L-phenylalanine methyl ester HCl (Phe, MW: 215.68) in the presence of EDC for 24 hours at room temperature. PEO-b-PGA was dissolved in 2 ml of DW. 26.42 mg (0.137 mmol) or 52.83 mg (0.275 mmol) of EDC were added to PEO-b-PGA aqueous solution to activate carboxylate groups. Simultaneously, 29.7 mg (0.137 mmol) or 59.4 mg (0.275 mmol) of Phe were added to the reacting solutions for 25% and 50% grafting, respectively. pH of the reacting solution was ca. pH 6.0. The resulting polymer, Phe-modified PEO-b-PPGA was dialyzed to remove byproduct, freeze-dried and characterized by $^1$H NMR (Varian 500 MHz spectrometer, $D_2O$)25° to determine the degree of grafting. Degrees of grafting were determined to 17% for PEO-b-PPGA25 and 30% for PEO-b-PPGA50, by comparing the integration ratios of methylene units in PEG (3.7 ppm) and phenyl groups (7.1-7.4 ppm) in $^1$H NMR, respectively.

Synthesis of Cross-Linked Micelles with Ionic Cores

Polymer micelles with cross-linked ionic cores were prepared by using block ionomer complex (BIC) of PEO-b-PPGA copolymer and divalent metal cations ($Ca^{2+}$) as templates by the previously described method with a slight modification (Bronich et al. (2005) J. Am. Chem. Soc., 127:8236-8237). In brief, PEO-b-PPGA/$Ca^{2+}$ complexes were prepared by mixing an aqueous solution of PEO-b-PPGA with a solution of $CaCl_2$ at a molar ratio of $[Ca^{2+}]/[COO^-]$=1.5. The EDC and Cys were then added to the dispersion of PEO-b-PPGA/$Ca^{2+}$ complexes. The reaction mixture was allowed to stir overnight at room temperature. The extent of degree of cross-linking was controlled by the ratio of amine functional groups to carboxylic acid groups. Byproducts of the cross-linking reaction and metal ions, which have cemented the ionic core, were removed by exhaustive dialysis of the reaction mixtures first, against 0.5% aqueous ammonia in the presence of EDTA, and then against distilled water. Finally, cross-linked (cl) PEO-b-PPGA micelles were obtained.

Turbidity Measurements

The turbidity measurements were carried out at 420 nm using a Perkin-Elmer Lambda 25 UV/VIS spectrophotometer after equilibration of the system for 3 minutes, which was proven to be sufficient for equilibration. The data are reported as (100–T)/100, where T is transmittance (%).

Determination of Particle Size and Zeta-Potential

Effective hydrodynamic diameter ($D_{eff}$) and ζ-potential of nanogels were determined using a Malvern Zetasizer (Malvern Instruments Ltd., Malvern, UK). All measurements were performed in automatic mode, at 25° C. Software provided by the manufacturer was used to calculate the size, polydispersity indices and ζ-potential of nanogels. The values were calculated from the measurements performed at least in triplicate.

Release Studies of DOX-Loaded Cross-Linked Micelles

The release of DOX from the cl-micelles was evaluated under the reductive environment by dialysis method using a membrane (MW cut-off 3,500 Da) in phosphate buffered saline (PBS, pH 7.4, 0.14 M NaCl). DOX was sampled at selected time intervals. The concentrations of DOX present in the dialysate were determined spectrophotometrically by measuring absorbance at 485 nm as described above. The concentration of DOX released from the micelles was expressed as a percentage of the total DOX available and plotted as a function of time.

Circular Dichroism (CD) Spectroscopy

The conformation of PGA-based copolymer and cl-micelles were examined in aqueous solutions by Aviv Circular Dichroism Model 202SF spectrometer (Lakewood, N.J.) equipped with a peltier temperature control system. Polymer solutions (50 μg/ml) were prepared with 10 mM phosphate buffer. Spectra of polymer solutions at pH 5.0 or pH 7.0 were recorded at 25° C. in the range of 200-260 nm in 1 nm increments using strain-free quartz cuvettes with a path length of 1.0 cm. Spectra were also obtained at different temperatures (25, 37 and 50° C.) in the range of 200-260 nm. Temperature induced unfolding of polymer solutions at pH 5.0 were conducted at a rate of 1° C./minute from 10° C. to 80° C. and CD changes were recorded at 222 nm. The reported spectra correspond to the average of at least three wavelength scans. Mean residual ellipticity ($[θ_{MRE}]$, deg $cm^2$/dmol) was calculated from equation (1):

$$[θ_{MRE}]=(θ)/10lcn \qquad (1)$$

Where (θ) is the measured ellipticity (mdeg), l is the path length (cm), c is the polymer molar concentration and n is the number of residues in the peptide. The α-helix contents were estimated from the molar ellipticity values using equation (2) (Morrow et al. (2000) Biochemistry, 39:11657-11666) and Dichroweb software (Whitmore et al. (2004) Nucleic Acids Res., 32:W668-673; Whitmore et al. (2008) Biopolymers 89:392-400).

$$α\text{-helix }(\%)=(-[θ_{MRE\ at\ 222\ nm}]+3000)/39000 \qquad (2)$$

Steady-State Fluorescence Studies

Fluorescence studies of various polymers and cl-micelles using pyrene and coumarin 153 (C153) were performed using a spectrofluorometer system (Flourlog®, HORIBA Jobin Yvon Inc., NJ, USA). First, steady-state fluorescence spectra of pyrene as the fluorescent probe were measured at excitation wavelength of 336 nm and all measurements were recorded with the bandwidth of 1 nm for excitation and emission. The known amounts of pyrene in acetone were added to empty vials, followed by acetone evaporation. Aqueous solutions of polymer samples were added to the vials. The pyrene concentration in the final solution was $6×10^{-7}$ M, the concentration slightly below the solubility of pyrene in water at 25° C. All measurements were studied at room temperature. Second, in separate experiment, 25 μl of coumarin 153 (C153) stock solution (1 mg/ml of concentration in acetone) was added to the vials, and evaporated. Each sample (1 mg/ml in 10 mM phosphate buffer at pH 7) were added to these vials and incubated for overnight. Steady-state fluorescence emission spectra of C153 were measured in aqueous solutions of polypeptides at excitation wavelength of 425 nm. Final concentration of C153 in solutions was 10 μg/ml. The peak emission wavelength of the sample spectrum was used for measurement of the fluorescence decay.

Time-Correlated Single-Photon Counting Spectroscopy (TCSPC)

Fluorescence lifetimes of C153 in various polypeptides and cl-micelles were determined using spectrofluorometer system (Flourlog®) with time-correlated single-photon counting spectroscopy (TCSPC) using NanoLED (Ex=460 nm) as the excitation source. TCSPC measurements were performed at same samples after measurements of steady-state spectroscopy of C153 in each sample. Fluorescence decay curves were accumulated to 10,000 counts in the peak channel of 4096 channels. Data was collected less than 2% of the source repetition rate to avoid photon pile up effects. The decay data as a function of time was analyzed using two exponential equation using DAS6 fluorescence decay analysis software.

Atomic Force Microscopy (AFM)

The AFM imaging was performed in air using a Multimode NanoScope IV system (Veeco, Santa Barbara, Calif.) operated in a tapping mode. The imaging was performed with regular etched silicon probes (TESP) with a spring constant of 42 N/m. For sample preparation, aqueous solutions of nanogels (5 μL, ca. 1.0 mg/ml) were deposited on positively charged 1-(3-aminopropyl)silatrane mica surface (APS-mica) for 2 minutes, followed by surface drying under argon atmosphere. The images were processed and the widths and heights of the particles were determined by using Femtoscan software (Advanced Technologies Center, Moscow, Russia).

Confocal Microscopy on Live Cell

Cellular uptake and localization studies of DOX-loaded cl-PEO-b-PPGA were conducted using live cell confocal microscope (Carl Zeiss LSM 510 Meta, Peabody, Mass.). MCF-7 human breast cancer cells ($1 \times 10^6$) were plated in live cell chambers (Fischer Scientific, Waltham, Mass.) and after two days (37° C., 5% $CO_2$) were exposed to DOX-loaded cl-PEO-b-PPGA for 45 minutes, followed by incubation with Lysotracker Red® for 5 minutes. Finally, cells were washed and kept in complete media for confocal imaging.

In Vitro Cytotoxicity Studies

Cytotoxicity of DOX-loaded cl-micelles was assessed in MCF-7 cells by a standard MTT assay as described (Kim et al. (2009) J. Control Release, 138:197-204). Briefly, cells were seeded in a 96-well microtiter plates with 5,000 cells per well and allowed to adhere for 24 hours prior to the assay. Cells were exposed to various doses (0-50 μg/ml on DOX basis) of DOX alone, polymer micelles alone, and DOX-loaded cl-micelles for 24 hours at 37° C., followed by washing with PBS, and maintaining in DMEM medium with 10% FBS for additional 72 hours. 25 μl of MTT indicator dye (5 mg/ml) was added to each well and the cells were incubated for 2 hours at 37° C. in the dark. 100 μl of 50% DMF-20% SDS solution was added to each well and kept overnight at 37° C. Absorption was measured at 570 nm in a microplate reader (SpectraMax® M5, Molecular Devices Co., USA) using wells without cells as blanks. All measurements were taken eight times. Based on the results of the test, the $IC_{50}$ values (the concentration which kill 50% of cells) were calculated by using GraphPad Prism Software (GraphPad Software, San Diego, Calif., USA).

Results

Preparation of Cross-Linked PEO-b-PPGA Micelles

Cross-linked micelles with hydrophobic moiety were synthesized via a two-step procedure schematically in FIG. 1. First, PEO-b-PPGA copolymers were self-assembled into BIC via condensation by $Ca^{2+}$ ions. Second, the cores of the BIC were cross-linked by the use of bifunctional agents (Bronich et al. (2005) J. Am. Chem. Soc., 127:8236-8237; Kim et al. (2009) J. Control Release 138:197-204). After completion of cross-linking reaction, the $Ca^{2+}$ ions and byproducts were removed by dialysis. Specifically, PEO-b-PPGA copolymers were reacted with $Ca^{2+}$ at pH 8.0 to create PEO-b-PPGA/$Ca^{2+}$ complexes. FIG. 2 presents turbidity of the PEO-b-PPGA/$Ca^{2+}$ complexes as a function of the charge ratio in the mixture, Z. Hydrophobized PEO-b-PPGA50 copolymers self-assemble with $Ca^{2+}$ to form BIC in the vicinity of ca. Z=2.0. The resulting BIC micelles showed ca. 30-40 nm of particle size over the entire range of the charge ratios studies in this study. In contrast, in case of PEO-b-PGA and PEO-b-PPGA25 with low degree of phenylalanine grafting, no complexes were formed by Z=6 due to the weak interactions of glutamic acid with $Ca^{2+}$ (Naoko Kono, A. I. (1966) Biopolymers 4:823-836). These results indicated that the stacking effect of the multiple phenyl groups in PGA backbone play an important role for the formation of poly(amino acid)/$Ca^{2+}$ complexes. Most of carboxylic groups in polyglutamic acid backbone is ionized at pH 8.0 because pKa of glutamic acid is ca. 4.4 (Li, C. (2002) Adv. Drug Deliv. Rev., 54:695-713). PGA is too hydrophilic and binding affinity with $Ca^{2+}$ is not so strong, but phenylalanine groups induced the increased packing and stability of the hydrophobic core. Remarkably, there is no precipitation in PEO-b-PPGA50/$Ca^{2+}$. Overall, the solution behavior of the resulting PEO-b-PGA complexes was dependent on the degree of grafting of phenylalanine.

Cross-linked micelles were synthesized using BIC formed by mixing an aqueous solution of PEO-b-PPGA with a solution of $CaCl_2$ at a molar ratio of Z=3.0. The resulting cl-PEO-b-PPGA micelles represented hydrophilic nanoparticles that comprised the hydrophilic PEO shell and ionic cores with hydrophobic moiety. To make sure cross-linking reaction, the resulting cl-PEO-b-PPGA micelles and PEO-b-PPGA copolymer were incubated with urea 8 M. Urea weakens the hydrophobic interactions between the polymer groups by unfolding process of hydrophobic groups which otherwise adopts a compact structure in pure water. The addition of urea 8 M to cl-PEO-b-PPGA micelles resulted in only a slight increase of size, showing successful cross-linking reaction. On contrast, the addition of urea 8 M to PEO-b-PPGA50 aqueous solution led to the dissociation of the self-assembled particles from 34 nm to ca 320 nm (polydispersity is close to 1), which indicates that all hydrophobic interaction was destroyed. In addition, the size of cl-PEO-b-PPGA micelles did not change even upon 100-fold dilution, which further confirmed successful covalent cross-linking of the micelles. The resulting polypeptide micelles appeared to be spherical shapes in tapping-mode AFM images (FIG. 3). The micelles were characterized with an average height of 10.3±0.15 nm and diameter of 27.7±0.17 nm. Aspect ratio (Width/Height) of 2.67 indicates the relative rigidity of micellar cores.

Swelling Behaviors of cl-PEO-b-PPGA Micelles

The resulting cl-PEO-b-PPGA nanogels showed pH-dependent swelling behavior. FIG. 4 demonstrated the effective diameter and ζ-potential of cl-PEO-b-PPGA micelles with 20% targeted degree of cross-linking as a function of pH. As pH increased, the particle size and net negative charge of cl-PEO-b-PPGA micelles increased considerably. Evidently, the swelling behavior was influenced by the ionization state of the carboxylic groups and secondary structure of the PGA chains of the micelles. PGA is known to form an alpha-helix secondary structure under acidic conditions and a random coil structure under basic conditions. Decrease of pH protonated carboxylates of PGA because apparent pKa value of carboxylate of PGA was ca. 5.4 and the intramolecular electrostatic repulsive forces are reduced as ionization of carboxylate groups in the PGA cores decreases, which allows for conformational transitions from random-coil to helix form (Abbruzzetti et al. (2000) Biophys J., 79:2714-2721).

In order to understand the effect of pH, temperature and hydrophobic amino acid on conformations of PGA-based polymer and cl-micelles, the secondary structure of the PGA backbones in various PGA-based copolymer and cl-PEO-b-PPGA micelles was further investigated using CD spectroscopy. FIG. 5 depicts typical CD-spectrum for PEO-b-PGA and cl-PEO-b-PPGA micelles at pH 5.0 and pH 7.0. CD spectrum for PEO-b-PGA copolymer displayed an alpha-helix with two minima at λ=207 and 222 nm at pH 5.0 and a random coil at pH 7, respectively. The CD intensity at 222 nm as an indicator of alpha-helix attenuated with increase of pH, indicating that alpha-helical formation of PGA polymers transformed to a random-coil structure (FIGS. 5 and 6). As calculated according to the equation 2 and Dichroweb software, the alpha helix (%) increased with decrease of pH around pH 5.3 (FIG. 7). These results are consistent with the behavior of PGA homopolymers as a positive control and those reported previously (Kašparová et al. (2004) Coll. Surfaces A: Physicochem. Eng. Aspects, 250:153-162; Inoue et al. (2005) J. Phys. Chem. B, 109:22623-22628). Interestingly, alpha-helix conformation of PEO-b-PGA at pH 5 was influenced by modification of phenylalanine. In CD spectrum of PEO-b-PPGA at pH 5, the minima at λ=207 was gradually disappeared with the increase of modification by phenylalanine and PEO-b-PPGA showed are similar spectrum as that of β-sheet spectrum which has a single negative band. This behavior could be explained by that steric bulk of phenylalanine might restrict the compact packing for alpha-helix formation of PGA backbone, because alpha helices are densely coiled structures through intramolecular hydrogen bonding (Adams et al. (2008) Biomacromolecules 9:2997-3003). Furthermore, temperature dependence on CD spectra of PEO-b-PGA and PEO-b-PPGA were evaluated at pH 5 (FIG. 8). Increase of temperature induced the depression of the negative CD spectrum. Compared to that of PEO-b-PGA copolymer, the CD spectra of PEO-b-PPGA were less attenuated, due to the difference from the increasing proportion of unordered conformations in the PGA chains. Notably, cl-PEO-b-PGA micelles and cl-PEO-b-PPGA micelles appeared to have same pH-dependent conformation transition as PEO-b-PGA and PEO-b-PPGA copolymer (FIG. 9). As shown in FIG. 4, these micelles had a relatively high net negative charge and maintained significant portion of the acid functionalities although some portion of the carboxylic groups were consumed during reaction. Therefore, the hydrogel-like behaviors of cl-PEO-b-PPGA micelles were affected by pH-dependent conformational change and ionization of PGA. Such an aspect of behavior is advantageous for the design of drug carriers with controlled loading and release characteristics.

Fluorescence Studies

The hydrophobicity and polarity of PGA-based block copolymer and cl-micelles was investigated by using pyrene and coumarin 153 (C153) as fluorescence probes. First, the intensity ratio of the first and third vibration emission peaks ($I_1/I_3$ ratio) in the fluorescence spectrum of pyrene was used to determine the polarity of the surrounding environment of the pyrene molecule at pH 7.0 (Bronich et al. (1999) Coll. Surfaces B: Biointerfaces, 16:243-251). $I_1/I_3$ ratios and the relative $I_1$ intensity of various polymers and cl-micelles at pH 7.0 were presented in FIG. 10. With the increase of the concentration of cl-PEO-b-PPGA micelles, the fluorescent intensity ($I_1$) of pyrene increased and the $I_1/I_3$ ratio undergoes a significant decrease, reflecting pyrene partitioning to micellar core. $I_1/I_3$ ratio for cl-PEO-b-PPGA micelles was changed even at a low concentration. While the $I_1/I_3$ values and $I_1$ intensity of PEO-b-PPGA block copolymer were changed above cmc values which formed self-assembled complexes due to their hydrophobic phenylalanine in the cores. On the other hand, PEO-b-PGA copolymer and PEO-b-PPGA25 with low hydrophobic moiety are very hydrophilic so that they could not form self-assembled nanoparticles at pH 7.0 at the concentration studied. The fluorescence ratio and intensity of both copolymers were almost close to those of buffer and not changed up to 3 mg/ml of concentration. Since $I_1/I_3$ values are dependent on the polarity of complexes, the lower $I_1/I_3$ values of cl-PEO-b-PPGA micelles reflected the formation of compact and hydrophobized cross-linked cores.

Figure 11:
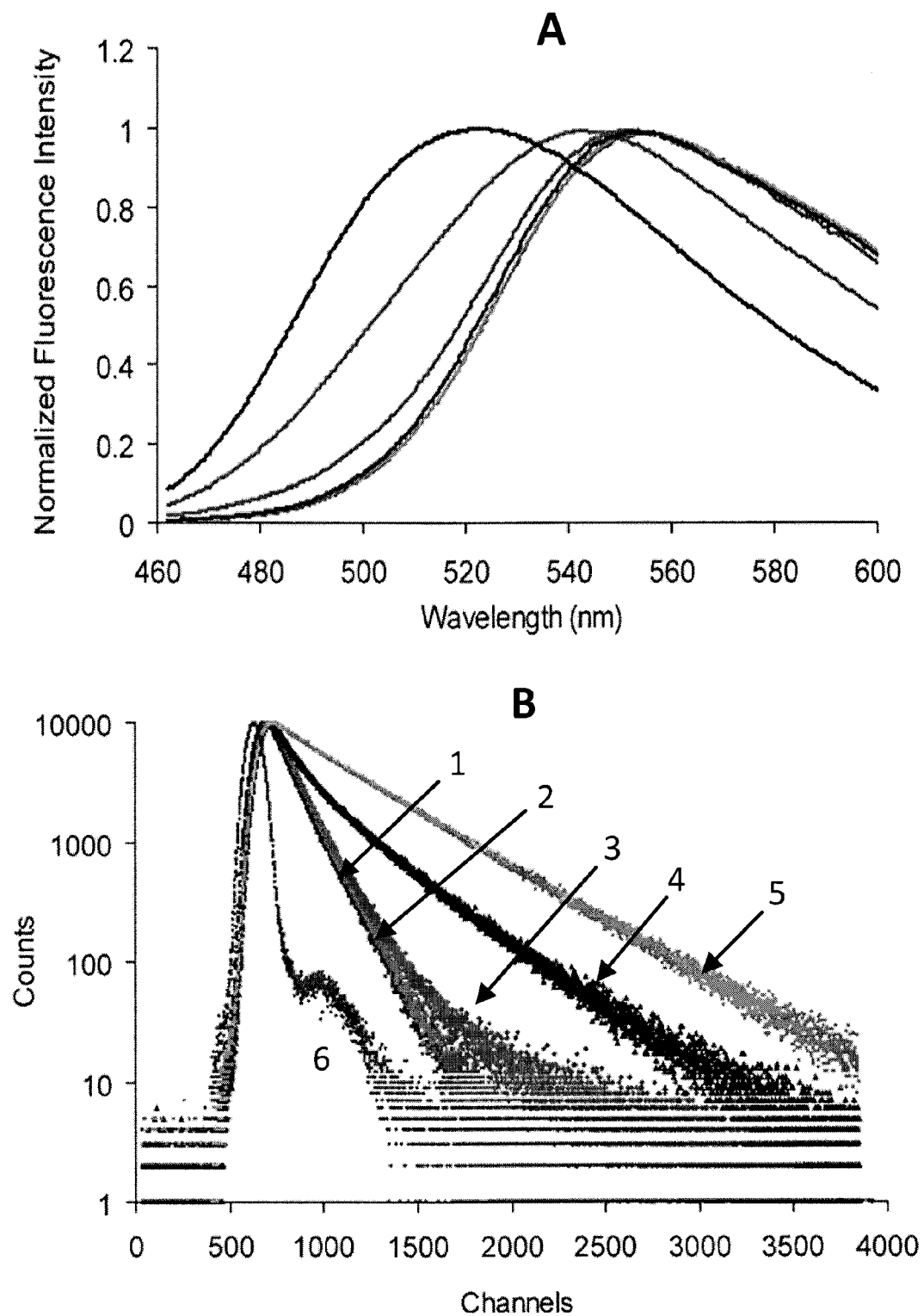

Furthermore, steady-state fluorescence and lifetime fluorescence of C 153 were measured in aqueous solutions of various PGA-based copolymer and cl-micelles (FIG. 11). C153 is used to determine the polarity of local solvent environment in the core of nanocarriers due to its unique solvatochromic behavior (Steege et al. (2007) Macromolecules 40:3739-3748; Jin et al. (2007) J. Phys. Chem. B, 111:7291-7302; Grant et al. (2005) Langmuir 21:1745-1752; Kumbhakar, M. (2007) J. Phys. Chem. B, 111:12154-12161). The emission wavelength of C153 is a sensitive reminder of the polarity of its local environment. Hydrophobic core in the PPGA micelles resulted in the blue-shift of the emission spectra of C153. This is attributed to a decrease in polarity as a consequence of modification of core by hydrophobic moiety. The maximum emission spectra of C153 in FIG. 11A showed the relative hydrophobicity of various polymer solutions, depending on the polarity of its local environment. In case of the cl-PEO-b-PPGA micelles, the maximum emission wavelength of C153 is 525 nm, indicating less polar environment around C153. Lifetime fluorescence was recorded from the samples at the emission maximum from C153 at 1 mg/ml of concentration (FIG. 11B). The results were fit using the lease-squares method to a two-exponential function and summarized in Table 1. cl-PEO-b-PPGA micelles showed the highest fluorescence lifetimes than buffer itself, PEO-b-PGA, PEO-b-PPGA25 or PEO-b-PPGA50, indicating increase of their hydrophobicity due to phenylalanine groups in the cross-linked cores. Increase of hydrophobicity resulted in the increase of T1 and T2 lifetimes. The blue-shift of maximum peaks and increase of lifetimes are attributed to a decrease in polarity as a result of modification of ionic core by hydrophobic moiety. In addition, the restricted penetration of polar waters toward cores containing hydrophobic phenylalanine may also contribute to decrease of polarity. The fluorescence lifetimes of C153 correlate well with steady-state fluorescence measurements corresponding to local polarity.

TABLE 1

Steady state maximum fluorescence wavelength and fluorescence lifetime of C153 in various PGA-based polymer and cl-micelles.

| Samples | buffer | PEO-b-PGA | PEO-b-PPGA25 | PEO-b-PPGA50 | cl-PEO-b-PPGA50 |
|---|---|---|---|---|---|
| Max. Emission Wavelength (nm) | 552.0 | 552.0 | 551.5 | 541.5 | 522.5 |
| T1 (ns) | 1.57 | 1.59 | 1.54 | 1.66 | 3.15 |
| T2 (ns) | 2.20 | 2.27 | 2.29 | 4.56 | 6.70 |
| T1 amplitude (%) | 85.2 | 79.1 | 80.2 | 57.4 | 19.8 |
| T2 amplitude (%) | 14.8 | 20.9 | 19.8 | 42.6 | 80.2 |

Loading and Release of DOX

DOX-loaded cl-PEO-b-PPGA micelles were prepared by mixing of DOX with the aqueous dispersion of the micelles at the feeding molar ratio of DOX to carboxylate groups (R=[DOX]/[COO-]=0.5) for 24 hours at pH 7.0 (Kim et al. (2009) J. Control Release 138:197-204). The net negative charge of the micelles was decreased from −50.7 mV to −22.7 mV as a result of the neutralization of the PPGA segments in the micelles due to the electrostatic interaction of DOX. This was also accompanied by a slight decrease in the particle size from ca. 72 nm to ca. 60 nm. The binding of DOX with the cores of cl-PEO-b-PPGA micelles was further supported by quenching of DOX fluorescence (by ca. 72%) compared to the fluorescence of free DOX in an aqueous solution (FIG. 12). The substantial quenching effect of fluorescence is likely due to π-π stacking interactions between DOX molecules bound to PPGA chains in the micelles through electrostatic interaction. The hydrophobic phenylalanine in cross-linked cores may also attribute to stacking interactions. Based on polymer amount added, loading capacity (drug/polymer w/w %) for DOX-loaded cl-PEO-b-PPGA micelles was ca. 30.4%.

It was of interest to investigate whether modification by hydrophobic moiety can modulate the DOX loading capacities of cross-linked micelles and release profile of the drug. DOX-loaded PEO-b-PPGA micelles without cross-linking and DOX-loaded cl-PEO-b-PGA without hydrophobic phenylalanine were prepared. After DOX loading, particle size and loading capacity (w/w %) were ca. 178 nm and 18.3% for PEO-b-PPGA50 micellar complexes and ca. 132 nm and 27.3% for cl-PEO-b-PGA, respectively. The drug release profiles were then evaluated in PBS buffer (pH 7.4, 0.14 M NaCl) at 37° C. using dialysis bag. As is seen in FIG. 13, the drug release profile from cl-micelles showed a distinct biphasic pattern with a relatively fast drug release within the first 8 hours followed by a slow release over 40 hours. However, cl-PEO-b-PPGA micelles with higher hydrophobic Phe had significantly a slower releasing rate of DOX than the release rates of DOX from non-cross-linked micelles or cross-linked micelles without hydrophobic Phe groups. For instance, at 8 hours PEO-b-PPGA50/DOX complexes and cl-PEO-b-PGA micelles without hydrophobic groups in the core released 77.9±4.1% and 75.4±3.7% of DOX, whereas cl-PEO-b-PPGA micelles released only 39.4±3.1% of DOX. From the release study, the difference in the release rate of DOX from various micelles could be caused by the cross-linked structure of the core-forming polymer and the difference of hydrophobicity in the cores. The encapsulation and release of DOX in PGA-based micellar nanocarriers were mainly governed by electrostatic interactions. Apart from electrostatic interactions between DOX and carboxylic groups in core-forming polymer, the cross-linking of PPGA as well as the hydrophobic stacking interaction of DOX and hydrophobized core-forming polymers could allow DOX to encapsulate and retain in the cores of cl-PEO-b-PPGA micelles, retarding the release of DOX.

Cellular Localization and in Vitro Cytotoxicity

The intracellular uptake of DOX-loaded cl-PEO-b-PPGA micelles as lysosomotropic drug carriers was evaluated in MCF-7 breast cancer cells. This was directly confirmed by significant co-localization of cl-micelles with a lysosomal marker, Lysotracker® Green in MCF-7 cancer cells (FIG. 4). DOX-loaded cl-PEO-b-PPGA micelles were internalized into the cells by a endocytic pathway and routed to lysosomes. This result is in good agreement with previous reports which delivers its cargo to lysosomal compartments (Chiu et al. (1997) J. Biomed. Mater. Res., 34:381-392). Indeed, polypeptide based on PGA can be degradated by lysosomal enzymes such as cathepsins, and lysosomal degradation of the polypeptides was enhanced by modification of carboxylic group of glutamic acid chain with hydrophobic amino acid such as phenylalanine (Chiu et al. (1997) J. Biomed. Mater. Res., 34:381-392). The confocal images showed that DOX-loaded cl-PEO-b-PPGA micelles reached to lysosomes and accumulation of polypeptides-based carriers could be avoided by degradation of drug-carrier in lysosomal environment. Based on the confocal result, it was of interest to evaluate whether such property can be useful and translated to the design of anti-cancer nanomedicines.

Next, the in vitro cytotoxcity of DOX-loaded cl-PEO-b-PPGA micelles in MCF-7 human breast cancer cells using MTT assay was evaluated. Calculated $IC_{50}$ values are summarized in Table 2. As expected, DOX-loaded cl-PEO-b-PPGA micelles displayed lower cytotoxic activity than free DOX, indicating their sustained release from cl-micelles. $IC_{50}$ values were incubation time dependent. Importantly, cl-PEO-b-PPGA micelles alone were not toxic at concentrations used for the treatment by DOX-loaded cl-micelles formulations.

TABLE 2

In vitro cytotoxicity of DOX-loaded cl-micelles in MCF-7 breast cancer cells (n = 4).

| | $IC_{50}$ (DOX equivalents in µg/mL) [a] | |
|---|---|---|
| Sample | 6 hours incubation | 24 hours incubation |
| Free DOX | 0.283 ± 0.049 | 0.046 ± 0.021 |
| DOX-loaded cl-PEO-A-PPGA [b] | 3.037 ± 0.085 | 0.179 ± 0.058 |

[a] $IC_{50}$ (µg/mL) represents the concentration of a drug for 50% inhibition in vitro.
[b] DOX-loaded cl-PEO-b-PPGA micelles with targeted degree of cross-linking of 20% were prepared at R = 0.5 and pH 7.0.

Cross-linked polypeptide micelles with hydrophobic amino acids in ionic cores based on PEO-b-Poly(L-glutamic acid) block copolymers were synthesized by utilizing self-assembled complexes of PEO-b-PPGA and $Ca^{2+}$ as templates for anticancer drug delivery. Such cross-linked micelles showed the hydrogel-like behaviors due to the protonation of carboxylic groups and pH-dependent conformation transition of PGA segments. The introduction of phenylalanine into PGA backbone resulted in the change of the alpha-helical conformation of PGA polypeptide and increase of hydrophobicity in the cores. DOX was successfully incorporated into the hydrophobized cross-linked ionic cores with high loading capacity (ca. 30 w/w %). Lysosome-specific internalization of DOX-loaded micelles may lead to pH-responsive release of DOX in solid tumor, because of the acidity of endosomes/lysosomes and eventually DOX accumulated in the nucleus. Therefore, this study demonstrated that biodegradable polypeptide micelles as efficient anticancer drug vehicles could be utilized by modifying the hydrophobicity of the cores. These biodegradable cross-linked polypeptide micelles with hydrophobic moiety are very promising for pharmaceutical and biomedical applications.

EXAMPLE 2

Synthesis of Hydrophobized PEO-b-Poly(L-glutamic Acid)

Poly(ethylene oxide)-block-poly(L-glutamic acid) (PEO-b-PGA) was synthesized using γ-benzyl-L-glutamate-N-carboxylic anhydride which was synthesized by the reaction of triphosgene (10 g, 33.7 mmol) with γ-benzyl-L-glutamate (20 g, 76.0 mmol) in 500 mL of anhydrous ethyl acetate. After reaction, the reaction mixture was allowed to reflux under argon for 3 hours, all solvent was evaporated. The resulting benzyl-glutamic acid-NCA was mixed with PEG in dimethylformamide (DMF). Benzyl protecting group of PEO-b-PGA was removed using trifluoroacetic acid (TFA). The repeating units of PGA and PEO were 150 and 114, on the basis of integral ratios of characteristic peaks of PGA and PEO in the $^1$H NMR spectra. Then, PEO-b-PGA (100 mg, 0.545 mmol as carboxylate groups) was hydrophobically modified by L-phenylalanine methyl ester HCl (PhA, MW: 215.68) in the presence of EDC for 24 hours at room temperature. PEO-b-PGA was dissolved in 2 ml of DW. 26.42 mg (0.137 mmol) and 52.83 mg (0.275 mmol) of EDC were added to PEO-b-PGA aqueous solution to activate carboxylate groups. Simultaneously, 29.7 mg (0.137 mmol) and 59.4 mg (0.275 mmol) of PhA were added to the reacting solutions for 25% and 50% grafting, respectively. pH of the reacting solution was ca. pH 6.2. The resulting polymer, PhA-modified PEO-b-PGA was dialyzed to remove byproduct, freeze-dried and characterized by $^1$H NMR to determine the degree of grafting. Degrees of grafting were determined to 17% and 30%, based on $^1$H NMR, respectively.

Synthesis of Hydrophobized PEO-b-PMA

PEO-b-Poly(methacrylic acid) (PEO-b-PMA) block copolymer was synthesized by atom transfer radical polymerization (ATRP) technique. PEO macroinitiator (PEO-Br) was synthesized by the esterification reaction of the hydroxyl end group of PEO monomethyl ether (25 g, 5.0 mmol) using 2-bromoisobutyryl bromide (3.45 g, 15.0 mmol) in the presence of TEA (1.01 g, 10.0 mmol). The diblock copolymer was synthesized by ATRP and the obtained PEO-b-PtBMA precursor was converted into PEO-b-PMA by hydrolysis in acidic solution. No signals of tert-butyl groups were observed from $^1$H-NMR, indicating complete hydrolysis of tert-butyl ester groups. The degree of polymerization was estimated to be 180 based on $^1$H NMR spectrum. To conjugate hydrophobic moiety (R) to PEO-b-PMA copolymer, NHS (4.5 mg, 0.04 mmol) and EDC (8.1 mg, 0.04 mmol) in $CH_2Cl_2$ (1.0 ml) were added to a solution of 100 mg PEO(170)-b-PMA(180) in 20 ml DMF/methanol (1:1 v/v) and stirred for 2 hours at room temperature. The fatty acid (or cholesterol, 0.04 mmol) in $CH_2Cl_2$ were added to this solution and the reaction mixture was stirred continuously for additional 24 hours. Organic solvents were evaporated in vacuum and resulting mixture was dialyzed against distilled water for 2 days using a dialysis membrane (MW cutoff 3,500 Da). Fatty acid (or cholesterol)-conjugated PEO-b-PMA was further purified using size exclusion chromatography and lyophilized.

Synthesis of Hydrophobized PEO-b-Poly(acrylic acid)

PEO-b-Poly(acrylic acid) (PEO-b-PAA) block copolymer was synthesized by atom transfer radical polymerization (ATRP) technique. The degree of polymerization was estimated to be 93 based on $^1$H NMR spectrum. To conjugate hydrophobic moiety (cholesterol) to PEO-b-PAA copolymer, NHS (4.5 mg, 0.04 mmol) and EDC (8.1 mg, 0.04 mmol) in $CH_2Cl_2$ (1.0 ml) were added to a solution of 100 mg PEO(114)-b-PAA(93) in 20 ml THF and stirred for 2 hours at room temperature. The cholesterol-ethylenediamine (0.04 mmol) in THF was added to this solution and the reaction mixture was stirred continuously for additional 24 hours. Organic solvents were evaporated in vacuum, and resulting mixture was dialyzed against distilled water for 2 days using a dialysis membrane (MW cutoff 3,500 Da). Cholesterol-conjugated PEO-b-PAA was further purified using size exclusion chromatography and lyophilized.

Complex Formation of Hydrophobized PEO-b-PGA with $Ca^{2+}$ Ions

Mixing of an aqueous solution of phenylalanine (Phe) modified-poly(ethylene oxide)-block-poly(L-glutamic acid) (PEO-b-PPGA) with a solution of $CaCl_2$ at molar ratio of $(Ca^{2+})/(COO^-)=1.5$ resulted in formation of slightly opalescent dispersions. Dynamic light scattering (DLS) measurements for the PEO-b-PPGA/$Ca^{2+}$ mixtures revealed the formation of block copolymer-metal complex micelles with diameters approximately 40 nm. The low polydispersity index (<0.1) suggested a narrow particle size distribution. The core of these micelles was composed of hydrophobized PGA chains neutralized by $Ca^{2+}$ ions and surrounded by a shell of PEO chains.

Cross-Linking of the Core of the PEO-b-PPGA/$Ca^{2+}$ Micelles

Cross-linking of the core of the micelles was achieved via condensation reactions between the carboxylic groups of PPGA and the amine functional groups of cystamine as biodegradable cross-linker in the presence of water-soluble carbodiimide. The EDC and Cys were then added to the dispersion of PEO-b-PPGA/$Ca^{2+}$ complexes. The percentage of cross-linking was 20% and was based on the stoichiometric ratio of amine functional groups to carboxylic acid groups. The reaction mixture was allowed to stir overnight at room temperature. By-products of the cross-linking reaction and metal ions, which have cemented the ionic core, were removed by exhaustive dialysis of the reaction mixtures first, against 0.5% aqueous ammonia in the presence of EDTA, and then against distilled water. As a result of the cross-linking reaction, narrowly distributed particles with a net negative charge (zeta-potential=−50 mV) and diameter of about 70 nm were present in the aqueous dispersion. No changes in the size of the particles were detected in the dispersion, even upon 100-fold dilution.

Preparation of Doxorubicin and/or Paclitaxel-Loaded Polymer Micelles

Doxorubicin was immobilized in the cross-linked polymer micelles by a mixing procedure using an aqueous dispersion of polymer micelles at pH 7. Upon loading with doxorubicin, the zeta-potential of the cross-linked polymer micelles increased from −40.5 mV to −22 mV indicating a decrease in the net negative charge. This indicates neutralization of the PPGA segments due to the binding of doxorubicin. Then, paclitaxel was loaded into doxorubicin-loaded micelles. Unbound agent is removed by, for example, ultrafiltration using Amicon YM30 centrifugal filter units (equipped with MWCO 30,000 membrane, Millipore), and the amount of the entrapped drugs in the micelles was determined using a HPLC systems. Loading of doxorubicin and paclitaxel to the polymer micelles also led to a slight increase of pm1icle size from about 72 nm to about 80 nm. The loading capacity of cross-linked micelles to bind doxorubicin and paclitaxel were 24.3% (w/w) and 8.3% (w/w), respectively. The loaded polymer micelles were stable in aqueous dispersions, exhibiting no aggregation even after several days.

Release Studies

Drug release kinetics was investigated in detail following a published procedure (Peracchia et al. (1997) J. Controlled Release 46:223-231). The doxorubicin-loaded polymer micelle in phosphate buffered saline (PBS) (pH 7.4, 2.0 mL) is placed into a dialysis bag (Spectra/Por-6, MWCO 3500) and immediately immersed in 25 mL of PBS kept at 37° C. The concentration of doxorubicin in the external solution is determined by UV-spectroscopy. Sustained release of drugs from combination micelles was observed.

Hydrophobized micelles with cross-linked cores that can incorporate multiple anticancer drugs, doxorubicin and paclitaxel, were successfully prepared. This system provided a single carrier system that simultaneously carried both drugs. These micelles were designed for sustained release drugs in physiological conditions. The drug loading and ratios in the micelles are also controllable by making appropriate modifications of the micelles preparation. Furthermore, cytotoxicity results for combination of doxorubicin and paclitaxel showed synergistic effect in human breast tumor models. Thus efficient and safe combination chemotherapy can be achieved by using the micelle formulation described herein.

Preparation of Doxorubicin and/or 17-AAG-Loaded Polymer Micelles

Doxorubicin and 17-N-allylamino-17-demethoxygeldanamycin (17-AAG) were immobilized in the cross-linked polymer micelles by a mixing procedure using an aqueous dispersion of polymer micelles at pH 7. Upon loading of both drugs, the size of cross-linked micelles was 86 nm. The loading capacity of cross-linked micelles to bind doxorubicin and 17-AAG were 31.4% (w/w) and 3.3% (w/w), respectively. The drug-loaded polymer micelles were stable in aqueous dispersions, exhibiting no aggregation even after several days.

17-AAG caused downregulation of HER2 expression and inhibited Ala activation in breast cancer cells that overexpress HER2. In addition, 17-AAG can lead to sensitization of human breast carcinoma cells to DOX and enhance the effect of DOX. The appropriately designed drug delivery vehicles such as cross-linked micelles with hydrophobic moiety maintain the drugs in the blood at much higher concentrations for extended periods of time and deliver them to the tumor. In vitro cytotoxicity results and in vivo antitumor results for combination of doxorubicin and 17-AAG showed synergistic effect in human breast tumor models. Thus efficient and safe combination chemotherapy can be achieved by using the micelle formulation described herein.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A micelle comprising
   a) at least one block copolymer comprising an ionically charged polymeric segment and a non-ionically charged polymeric segment, wherein said ionically charged polymeric segment is grafted with hydrophobic moieties as side chains of said ionically charged polymeric segment, wherein said ionically charged polymeric segment is cross-linked and forms the core of the micelle, and wherein said non-ionically charged polymeric segment is hydrophilic; and
   b) at least one bioactive agent.

2. The micelle of claim 1, wherein said bioactive agent is a therapeutic agent or a chemotherapeutic agent.

3. The micelle of claim 1, wherein said non-ionically charged polymeric segment comprises polyethylene oxide.

4. The micelle of claim 1, wherein said ionically charged polymeric segment is a polyamino acid.

5. The micelle of claim 4, wherein said polyamino acid is polyglutamic acid.

6. The micelle of claim 5, wherein said hydrophobic moiety is selected from the group consisting of a hydrophobic small molecule, lipid, fatty acid, cholesterol, and a hydrophobic amino acid.

7. The micelle of claim 5, wherein said hydrophobic moiety is a hydrophobic amino acid.

8. The micelle of claim 7, wherein said hydrophobic amino acid is phenylalanine.

9. The micelle of claim 1, wherein said hydrophobic moiety is selected from the group consisting of a hydrophobic small molecule, lipid, fatty acid, cholesterol, and a hydrophobic amino acid.

10. The micelle of claim 9, wherein said hydrophobic amino acid is phenylalanine.

11. The micelle of claim 1, wherein said micelle is linked to at least one targeting ligand.

12. The micelle of claim 1, wherein said micelle comprises at least two bioactive agents.

13. The method of claim 12, wherein at least one bioactive agent is hydrophobic and at least one bioactive agent is charged.

14. A composition comprising the micelle of claim 1 and at least one pharmaceutically acceptable carrier.

15. The micelle of claim 1, wherein said bioactive agent is stabilized within the core by non-covalent electrostatic, hydrophobic, or nonpolar interactions.

16. The micelle of claim 1, wherein said hydrophobic moiety has a molecular weight less than 1 kDa.

17. The micelle of claim 1, wherein the degree of grafting of the hydrophobic moiety is at least 20%.

* * * * *

SEQUENCE LISTING

<160> NUMBER OF SEQ ID NOS: 1

<210> SEQ ID NO 1
<211> LENGTH: 150
<212> TYPE: PRT
<213> ORGANISM: Artificial Sequence
<220> FEATURE:
<223> OTHER INFORMATION: Synthetic sequence

<400> SEQUENCE: 1

Glu Glu Glu Glu Glu Glu Glu Glu Glu Glu Glu Glu Glu Glu Glu Glu
 1               5                   10                  15

Glu Glu Glu Glu Glu Glu Glu Glu Glu Glu Glu Glu Glu Glu Glu Glu
            20                  25                  30

Glu Glu Glu Glu Glu Glu Glu Glu Glu Glu Glu Glu Glu Glu Glu Glu
        35                  40                  45

Glu Glu Glu Glu Glu Glu Glu Glu Glu Glu Glu Glu Glu Glu Glu Glu
    50                  55                  60

Glu Glu Glu Glu Glu Glu Glu Glu Glu Glu Glu Glu Glu Glu Glu Glu
65                  70                  75                  80

Glu Glu Glu Glu Glu Glu Glu Glu Glu Glu Glu Glu Glu Glu Glu Glu
                85                  90                  95

Glu Glu Glu Glu Glu Glu Glu Glu Glu Glu Glu Glu Glu Glu Glu Glu
            100                 105                 110

Glu Glu Glu Glu Glu Glu Glu Glu Glu Glu Glu Glu Glu Glu Glu Glu
        115                 120                 125

-continued

```
Glu Glu Glu Glu Glu Glu Glu Glu Glu Glu Glu Glu Glu Glu
    130             135             140
Glu Glu Glu Glu Glu Glu
145             150
```